(12) United States Patent
Frank et al.

(10) Patent No.: US 11,446,331 B2
(45) Date of Patent: Sep. 20, 2022

(54) WOUND HEALING AND TISSUE ENGINEERING

(71) Applicants: The United States Government as Represented by the Department of Veterans Affairs, Washington, DC (US); The Brigham and Women's Hospital, Inc., Boston, MA (US); Children's Medical Center Corporation, Boston, MA (US)

(72) Inventors: Markus H. Frank, Cambridge, MA (US); Natasha Y. Frank, Cambridge, MA (US); Dennis P. Orgill, Belmont, MA (US); George F. Murphy, Boston, MA (US)

(73) Assignees: The Brigham and Women's Hospital, Inc., Boston, MA (US); Children's Medical Center Corporation, Boston, MA (US); The United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/890,251

(22) PCT Filed: May 9, 2014

(86) PCT No.: PCT/US2014/037435
§ 371 (c)(1),
(2) Date: Nov. 10, 2015

(87) PCT Pub. No.: WO2014/182994
PCT Pub. Date: Nov. 13, 2014

(65) Prior Publication Data
US 2016/0106782 A1    Apr. 21, 2016

Related U.S. Application Data

(60) Provisional application No. 61/822,134, filed on May 10, 2013.

(51) Int. Cl.
| | | |
|---|---|---|
| A61K 35/28 | (2015.01) | |
| C12N 5/0775 | (2010.01) | |
| A61L 27/26 | (2006.01) | |
| A61L 27/38 | (2006.01) | |
| A61L 27/54 | (2006.01) | |
| A61L 27/56 | (2006.01) | |
| C12N 5/071 | (2010.01) | |
| A61K 38/00 | (2006.01) | |

(52) U.S. Cl.
CPC .............. *A61K 35/28* (2013.01); *A61L 27/26* (2013.01); *A61L 27/3834* (2013.01); *A61L 27/3886* (2013.01); *A61L 27/54* (2013.01); *A61L 27/56* (2013.01); *C12N 5/063* (2013.01); *C12N 5/0668* (2013.01); *A61K 38/00* (2013.01); *A61L 2430/16* (2013.01); *A61L 2430/34* (2013.01); *A61L 2430/40* (2013.01); *C12N 2533/30* (2013.01); *C12N 2533/54* (2013.01); *C12N 2533/70* (2013.01)

(58) Field of Classification Search
None
See application file for complete search history.

(56) References Cited

U.S. PATENT DOCUMENTS

| | | | |
|---|---|---|---|
| 4,382,441 A | 5/1983 | Svedman | |
| 4,817,594 A | 4/1989 | Juhasz | |
| 5,434,075 A | 7/1995 | Mechetner et al. | |
| 5,759,570 A | 6/1998 | Arnold | |
| 5,833,641 A | 11/1998 | Curtis et al. | |
| 5,904,659 A | 5/1999 | Duarte et al. | |
| 5,906,934 A | 5/1999 | Grande et al. | |
| 6,152,142 A | 11/2000 | Tseng | |
| 6,355,239 B1 | 3/2002 | Bruder et al. | |
| 6,387,367 B1 | 5/2002 | Davis-Sproul et al. | |
| 6,464,983 B1 | 10/2002 | Grotendorst | |
| 6,541,024 B1 | 4/2003 | Kadiyala et al. | |
| 6,673,606 B1 | 1/2004 | Gian et al. | |
| 6,755,807 B2 | 6/2004 | Risk, Jr. et al. | |
| 6,797,269 B2 | 9/2004 | Mosca et al. | |
| 6,846,883 B2 | 1/2005 | Frank et al. | |
| 6,875,430 B2 | 4/2005 | McIntosh et al. | |
| 6,905,678 B2 | 6/2005 | Havenga et al. | |
| 7,029,666 B2 | 4/2006 | Bruder et al. | |
| 7,465,554 B2 | 12/2008 | Frank et al. | |

(Continued)

FOREIGN PATENT DOCUMENTS

| | | |
|---|---|---|
| JP | 2006-519681 A1 | 8/2006 |
| WO | WO 2007/138334 A1 | 12/2007 |

(Continued)

OTHER PUBLICATIONS

Shafiq et al "Decellularized human cornea for reconstructing the corneal epithelium and anterior stroma" Tissue Engineering: Part C, vol. 18, No. 5, 2012, pp. 340-348.*
Zheng et al, "Mesenchymal stem cells on a decellularized cartilage matrix for cartilage tissue engineering" Biotechnology and Bioprocess Engineering, vol. 16, 20111, pp. 593-602.*
Dua et al, "The amniotic membrane in ophthalmology" 2004, 49(1):51-57. (Year: 2004).*
Akle et al, "Permeability of the amniotic membrane and its potential application for transplantation purposes" Biological Research in Pregnancy, 1981, vol. 2, No. 1 pp. 23-27. (Year: 1981).*

(Continued)

*Primary Examiner* — Allison M Fox
(74) *Attorney, Agent, or Firm* — Wolf, Greenfield & Sacks, P.C.

(57) ABSTRACT

The present invention is directed to wound healing scaffolds cografted with a population of stem cells, wherein the population of stem cells are ABCB5+ stem cells. The scaffolds are, for instance, collagen glycosaminoglycan scaffolds.

10 Claims, 17 Drawing Sheets

(56) References Cited

U.S. PATENT DOCUMENTS

| | | | |
|---|---|---|---|
| 7,928,202 | B2 | 4/2011 | Frank et al. |
| 8,076,091 | B2 | 12/2011 | Frank et al. |
| 8,288,378 | B2 | 10/2012 | Kim et al. |
| 8,425,876 | B2 | 4/2013 | Frank et al. |
| 8,455,245 | B2 | 6/2013 | Frank |
| 8,507,273 | B2 | 8/2013 | Frank et al. |
| 8,697,072 | B2 | 4/2014 | Frank et al. |
| 9,266,946 | B2 | 2/2016 | Frank et al. |
| 9,561,264 | B2 | 2/2017 | Frank et al. |
| 9,801,912 | B2 | 10/2017 | Frank et al. |
| 9,855,342 | B2 | 1/2018 | Frank et al. |
| 9,879,226 | B2 | 1/2018 | Dong-Sam et al. |
| 10,017,738 | B2 | 7/2018 | Frank |
| 10,316,085 | B2 | 6/2019 | Frank et al. |
| 11,129,854 | B2 | 9/2021 | Frank et al. |
| 2001/0007658 | A1 | 7/2001 | Usala et al. |
| 2002/0037522 | A1 | 3/2002 | Frank et al. |
| 2002/0068913 | A1 | 6/2002 | Fleischmann |
| 2002/0127736 | A1 | 9/2002 | Chou et al. |
| 2002/0150720 | A1 | 10/2002 | Howard et al. |
| 2004/0175366 | A1 | 9/2004 | Badylak |
| 2005/0049185 | A1 | 3/2005 | Frank et al. |
| 2005/0249728 | A1 | 11/2005 | Singh et al. |
| 2007/0116691 | A1 | 5/2007 | Cambier et al. |
| 2008/0003206 | A1* | 1/2008 | Frank .................. C12N 5/0668 424/93.21 |
| 2008/0132423 | A1 | 6/2008 | Kondo |
| 2009/0117117 | A1 | 5/2009 | Frank et al. |
| 2009/0162873 | A1 | 6/2009 | Frank et al. |
| 2010/0145030 | A1 | 6/2010 | Frank et al. |
| 2011/0165149 | A1 | 7/2011 | Frank et al. |
| 2011/0287034 | A1 | 11/2011 | Frank et al. |
| 2012/0034196 | A1 | 2/2012 | Frank et al. |
| 2013/0017175 | A1* | 1/2013 | Bartholomew ........ A61K 35/28 424/93.7 |
| 2013/0287785 | A1 | 10/2013 | Frank et al. |
| 2013/0315880 | A1 | 11/2013 | Frank |
| 2014/0302031 | A1 | 10/2014 | Frank et al. |
| 2015/0374756 | A1 | 12/2015 | Frank et al. |
| 2016/0009804 | A1 | 1/2016 | Frank et al. |
| 2016/0136297 | A1 | 5/2016 | Frank et al. |
| 2018/0064762 | A1 | 3/2018 | Frank et al. |
| 2018/0320131 | A1 | 11/2018 | Frank |
| 2020/0385464 | A1 | 12/2020 | Frank et al. |
| 2021/0095254 | A1 | 4/2021 | Frank et al. |
| 2021/0188999 | A1 | 6/2021 | Frank |

FOREIGN PATENT DOCUMENTS

| | | | |
|---|---|---|---|
| WO | WO 2007/143139 | A1 | 12/2007 |
| WO | WO 2010/065711 | A1 | 6/2010 |
| WO | WO 2010/133853 | A1 | 11/2010 |
| WO | WO 2013/002953 | A1 | 1/2013 |
| WO | WO 2014/130518 | A1 | 8/2014 |
| WO | WO 2014/182994 | A1 | 11/2014 |
| WO | WO 2016/179576 | A1 | 11/2016 |

OTHER PUBLICATIONS

"Mesh" Definition from Merriam-Webster Online dictionary. Retrieved Nov. 26, 2018 from URL: https://www.merriam-webster.com/dictionary/mesh (Year: 2018).*

International Preliminary Report on Patentability for PCT/US2014/037435 dated Nov. 19, 2015.

International Search Report and Written Opinion for PCT/US2014/037435 dated Aug. 18, 2014.

Extended European Search Report for European Application No. 14795146.1 dated Nov. 18, 2016.

Cotsarelis et al., Existence of slow-cycling timbal epithelial basal cells that can be preferentially stimulated to proliferate: implications on epithelial stem cells. Cell. Apr. 21, 1989;57(2):201-9.

Eveleth, Cell-based therapies for ocular disease. J Ocul Pharmacol Ther. Dec. 2013;29(10):844-54. doi: 10.1089/jop.2013.0028. Epub Sep. 19, 2013.

Frank et al. 2005, ABCB5-mediated doxorubicin transport and chemoresistance in human malignant melanoma. Cancer Research. 65:10;4320-4333.

Frank et al., ABCB5 P-glycoprotein is a molecular marker of the Hoechst 33342 side population phenotype among human fetal skeletal muscle cells. FASEB Journal. 2004;18(4-5):A183. Abstract 144.9.

Frank et al., Immunomodulatory functions of mesenchymal stem cells. Lancet. May 1, 2004;363(9419):1411-2.

Frank et al., Regulation of progenitor cell fusion by ABCB5 P-glycoprotein, a novel human ATP-binding cassette transporter. J Biol Chem. Nov. 21, 2003;278(47):47156-65. Epub Sep. 7, 2003.

Frank et al., Specific MDR1 P-glycoprotein blockade inhibits human alloimmune T cell activation in vitro. J Immunol. Feb. 15, 2001;166(4):2451-9.

Frank et al., VEGFR-1 expressed by malignant melanoma-initiating cells is required for tumor growth. Cancer Res. Feb. 15, 2011;71(4):1474-85. Epub Jan. 6, 2011.

Frassoni et al., Cord blood transplantation provides better reconstitution of hematopoietic reservoir compared with bone marrow transplantation. Blood. Aug. 1, 2003;102(3):1138-41. Epub Apr. 10, 2003.

Goodell et al., Isolation and functional properties of murine hematopoietic stem cells that are replicating in vivo. J Exp Med. Apr. 1, 1996;183(4):1797-806.

Guerci et al., Predictive value for treatment outcome in acute myeloid leukemia of cellular daunorubicin accumulation and P-glycoprotein expression simultaneously determined by flow cytometry. Blood. Apr. 15, 1995;85(8):2147-53.

Hierner et al., Skin grafting and wound healing-the "dermato-plastic team approach". Clin Dermatol. Jul.-Aug. 2005;23(4):343-52.

Jorgensen et al., Engineering mesenchymal stem cells for immunotherapy. Gene Ther. May 2003;10(10):928-31.

Juncosa-Melvin et al., The effect of autologous mesenchymal stem cells on the biomechamcs and histology of gel-collagen sponge constructs used for rabbit patellar tendon repair. Tissue Eng. Feb. 2006;12(2):369-79.

Kim et al, Identification of human ABCB5(+) dermal progenitor cells with multipotent differentiation plasticity. Apr. 1, 2010;130(Suppl 1):S107. Abstract.

Kleffel et al., ABCB5 inhibition sensitizes Merkel cell carcinoma cells to chemotherapy-induced apoptosis. J Invest Dermatol. 2014;134:S18. Meeting abstract.

Kobayahsi et al., In vitro response of the bone marrow-derived mesenchymal stem cells seeded in a type-I collagen-glycosaminoglycan scaffold for skin wound repair under the mechanical loading condition. Mol Cell Biomech. Dec. 2009;6(4):217-27.

Ksander et al., ABCB5 is a limbal stem cell gene required for corneal development and repair. Nature. Jul. 17, 2014;511(7509):353-7. doi: 10.1038/nature13426. Epub Jul. 2, 2014.

Meier et al., Progressive decrease in number and change in niche preference of the ABCB5(+) mesenchymal stem cell subset in the skin during aging. Sep. 1, 2010;130(Suppl. 2):S88. Abstract.

Menke et al., Expression analysis of multidrug efflux pump genes in mouse hematopoietic stem and progenitor cells. Blood. 1999;94(10)(Supp 1, Part 1):Abstract #132.

Pendse et al., P-Glycoprotein Functions as a Differentiation Switch in Antigen Presenting Cell Maturation. Am J Transplant Dec. 2008; 6(12):2884-93.

Schatton et al., The Chemoresistance Mediator ABCB5 Identifies Melanoma Stem Cells. 14th SPORE Investigator's Workshop. 2006:92. Abstract 150.

Schatton et al., ABCB5 Identifies Immunoregulatory Dermal Cells. Cell Rep. Sep. 8, 2015;12(10):1564-74. doi: 10.1016/j.celrep.2015.08.010.

Setia et al., Profiling of ABC transporters ABCB5, ABCF2 and nestin-positive stem cells in nevi, in situ and invasive melanoma. Mod Pathol. Aug. 2012;25(8):1169-75. doi: 10.1038/modpathol.2012.71. Epub May 4, 2012.

Sharom, The P-glycoprotein efflux pump: how does it transport drugs? J Membr Biol. Dec. 1, 1997;160(3):161-75.

(56) References Cited

OTHER PUBLICATIONS

Shi et al., Transplantation of dermal multipotent cells promotes the hematopoietic recovery in sublethally irradiated rats. J Radiat Res (Tokyo). Mar. 2004;45(1):19-24.

Tatpalensuu et al., Correlation of gene expression of ten drug efflux proteins of the ATP-binding cassette transporter family in normal human jejunum and in human intestinal epithelial Caco-2 cell monolayers. J Pharmacol Exp Ther. Oct. 2001;299(1):164-70.

Thill et al., Expression of CD 133 and other putative stem cell markers in uveal melanoma. Melanoma Res. Oct. 2011;21(5):405-16.

Vrana et al., Development of a reconstructed cornea from collagen-chondroitin sulfate foams and human cell cultures. Invest Ophthalmol Vis Sci. Dec. 2008;49(12):5325-31. doi: 10.1167/iovs.07-1599. Epub Aug. 15, 2008.

Wilson et al., ABCB5 identifies a therapy-refractory tumor cell population in colorectal cancer patients. Cancer Res. Aug. 1, 2011;71(15):5307-16. Epub Jun. 7, 2011.

Young et al., Adult-derived stem cells and their potential for use in tissue repair and molecular medicine. J Cell Mol Med. Jul.-Sep. 2005;9(3):753-69.

Young et al., Human pluripotent and progenitor cells display cell surface cluster differentiation markers CD10, CD13, CD56, and MHC class-I. Proc Soc Exp Biol Med. May 1999;221(1):63-71.

Zhong et al., Tissue scaffolds for skin wound healing and dermal reconstruction. Wiley Interdiscip Rev Nanomed Nanobiotechnol. Sep.-Oct. 2010;2(5):510-25. doi: 10.1002/wnan.100.

Formigli et al. Dermal matrix scaffold engineered with adult mesenchymal stem cells and platelet-rich plasma as a potential tool for tissue repair and regeneration. J Tissue Eng Regen Med. Feb. 2012;6(2):125-34.

Herbst et al. Monoclonal antibodies to target epidermal growth factor receptor-positive tumors: a new paradigm for cancer therapy. Cancer. Mar. 1, 2002;94(5):1593-611.

Liu et al., Tissue-engineered skin containing mesenchymal stem cells improves burn wounds. Artif Organs. Dec. 2008;32(12):925-31.

Meruane et al. The use of adipose tissue-derived stem cells within a dermal substitute improves skin regeneration by increasing neoangiogenesis and collagen synthesis. Plast Reconstr Surg. Jul. 2012;130(1):53-63. doi: 10.1097/PRS.0b013e3182547e04.

Milenic et al. Cetuximab: preclinical evaluation of a monoclonal antibody targeting EGFR for radioimmunodiagnostic and radioimmunotherapeutic applications. Cancer Biother Radiopharm. Oct. 2008;23(5):619-31. doi: 10.1089/cbr.2008.0493.

Pellegrini et al. p63 identifies keratinocyte stem cells. Proc Natl Acad Sci U S A. Mar. 13, 2001;98(6):3156-61.

Japanese Office Action dated Jan. 26, 2018 from Japanese Application No. 2016-513108.

Japanese Office Action dated Dec. 17, 2018 for JP App. No. 2016-513108.

Yamaoka., Biological Scaffolds. Artificial Organs, 2011, vol. 40, No. 3, pp. 231-235.

International Search Report and Written Opinion for PCT/US2019/029235 dated Sep. 25, 2019.

Moitra et al., Molecular evolutionary analysis of ABCB5: the ancestral gene is a full transporter with potentially deleterious single nucleotide polymorphisms. PLoS One. Jan. 27, 2011;6(1):e16318.

Woodward et al., Corneal donor tissue preparation for endothelial keratoplasty. J Vis Exp. Jun. 12, 2012;(64):e3847.

\* cited by examiner

From: Fig. 11A  From: Fig. 11A

WOUND HEALING AND TISSUE ENGINEERING

RELATED APPLICATIONS

This application is a national stage filing under U.S.C. § 371 of PCT International Application PCT/US2014/037435, entitled "WOUND HEALING AND TISSUE ENGINEERING", with an international filing date of May 9, 2014, which claims priority under 35 U.S.C. § 119(e) to U.S. Provisional Application Ser. No. 61/822,134, entitled "WOUND HEALING AND TISSUE ENGINEERING" filed on May 10, 2013, which are herein incorporated by reference in their entirety.

GOVERNMENT LICENSE RIGHTS

This invention was made with government support under CA113796 awarded by The National Institutes of Health. The government has certain rights in the invention.

FIELD OF INVENTION

The present invention is directed at methods and compositions for wound healing and tissue engineering, involving ABCB5 positive stem cells in collagen glycosaminoglycan scaffolds.

BACKGROUND OF INVENTION

Regenerative medicine involves the repair, regeneration, maintenance, and replacement of tissues and organs using exogenous materials such as scaffolds. The scaffolds may be seeded with cells, such as primary cells or stem cells, and various factors to encourage tissue growth. However, a number of challenges remain in the design of appropriate material for regenerative medicine and tissue engineering.

Over one million new chronic wounds develop in the United States each year with estimated treatment costs reaching into the billions of dollars. Wounds can be conceptualized as defects in the protective covering of an individual organ or organ system. Without this physiological barrier, the tissue normally protected by the covering is subject to loss of biologic compartmentalization. When tissue is no longer physiologically compartmentalized it is subject to fluid loss, invasion by microorganisms, electrolyte imbalances, and in some cases metabolic dysfunction. Fluids lost by non-compartmentalized tissue include but are not limited to: blood, plasma, lymph, enteric contents, bile, cerebral spinal fluid, mucus. These fluid losses lead to desiccation of the underlying tissue and enable invasion by microorganisms, leading to potential infection and, in many cases, progressive tissue loss. For example, the inability to heal a chronic skin wound on the lower extremity may lead to amputation of either a portion or all of the effected limb. There are several etiologies for such chronic lower extremity skin wounds, including mechanical trauma, burns, radiation, arterial insufficiency, venous stasis, chronic infection, neuropathy, and systemic diseases such as diabetes. Current methods for improving wound healing emphasize effective drainage, prevention of infection, reduction of inflammation and minimization of tissue and fluid loss.

Chronic cutaneous wounds pose significant health problems for patients with diverse medical conditions such as diabetes, burns, trauma such as wartime-sustained trauma, spinal cord injury, and vascular insufficiency. Some of these patients are at risk of developing chronic wounds as a consequence of immobility and pressure ulcers as well as chronic non-healing ulcers due to diabetes or peripheral vascular disease. The default response to injury in postnatal human skin is driven by the necessity of rapid wound closure and is destined to result in formation of a scar. While scars are sufficient for restoration of skin barrier function, they often impair other normal functions by replacing essential cutaneous structures with connective tissue. In fetal life, a more protected environment in which developing skin is bathed in sterile amniotic fluid, the human integument is fully capable of scarless regeneration, i.e. regenerative wound healing. Current understanding of the inherent plasticity of adult stem cells suggests that this phenomenon may be replicated post-natally.

SUMMARY OF INVENTION

The present invention incorporates and is based at least in part upon the discovery that stem cells that express ABCB5 show differentiation plasticity and further enhance wound healing and/or tissue regeneration when employed alone or in the context of biodegradable scaffolds.

In some aspects the invention is a wound healing scaffold comprised of a collagen glycosaminoglycan scaffold cografted with a population of stem cells, wherein at least 80% of the population of stem cells are ABCB5+ stem cells.

In other aspects the invention is a wound healing scaffold comprised of a collagen glycosaminoglycan scaffold cografted with a population of stem cells, less than 50% of the cells of the composition are ABCB5(−) cells.

In yet other aspects the invention is a wound healing scaffold comprised of a collagen glycosaminoglycan scaffold cografted with a population of ABCB5+ stem cells, wherein the cell population includes less than 5% keratinocytes and/or epidermal cells.

A wound healing scaffold comprised of a collagen glycosaminoglycan scaffold cografted with a population of ABCB5+ ocular stem cells, wherein the cell population is free of non-ocular cells is provided in other aspects of the invention.

A wound healing scaffold comprised of a collagen glycosaminoglycan scaffold cografted with a population of ABCB5+ stem cells isolated from a tissue of a subject, wherein the ABCB5+ stem cells have been separated from other cells in the subject using an antibody specific for ABCB5 is provided in other aspects.

The ABCB5+ stem cells may be ABCB5+ dermal mesenchymal stem cells. In some embodiments at least 85% or 90% of the population of stem cells are ABCB5+ stem cells.

In some embodiments the scaffold is a porous matrix of cross-linked collagen and glycosaminoglycan. The collagen may be, for instance, bovine tendon collagen. In some embodiments the glycosaminoglycan is selected from the group consisting of chondroitin 6-sulfate, chondroitin 4-sulfate, heparin, heparin sulfate, keratin sulfate, dermatan sulfate, and combinations thereof.

The scaffold may include a semi-permeable layer such as polysiloxane (silicone). In other embodiments the scaffold is a mesh scaffold. Optionally the scaffold may be shaped for insertion into a tissue.

In some embodiments the scaffold is INTEGRA® Meshed Bilayer Wound Matrix.

The scaffold may have a varying pore size. For instance, the scaffold may have a pore size of about 10-500 or about 50-350 or about 70-200 micrometers.

The scaffold may include at least one bioactive molecule effective to enhance wound healing. For instance, the bioactive molecule may be a member selected from the group consisting of growth factors, anti-inflammatory agents, wound healing agents, anti-scarring agents, antimicrobial agents, cell adhesion peptides, tissue generation modulating cells, nucleic acids, nucleic acid analogues, proteins, peptides, amino acids, ceramic, and combinations thereof.

In some embodiments the scaffold is sized as 2 in×2 in (25 sq cm), 4 in×5 in (125 sq cm), 4 in×10 in (250 sq cm), or 8 in×10 in (500 sq cm).

A method for promoting wound healing, by contacting a wound with the wound healing scaffold described herein in order to promote healing is provided in other aspects of the invention. In some embodiments the contacting comprises applying the composition to a hemorrhaging site to control bleeding.

In some embodiments the wound is a burn or a diabetic ulcer.

In some embodiments a negative pressure wound therapy is used with the scaffold.

In other embodiments the method may involve subsequently securing the wound with a medically acceptable covering to treat the wound.

The wound may be selected from the group consisting of: partial and full-thickness wound, pressure ulcers, venous ulcers, diabetic ulcers, chronic vascular ulcers, tunneled/undermined wounds, surgical wounds, trauma wounds, and draining wounds.

The invention in other aspects is a method for tissue engineering, by seeding a collagen glycosaminoglycan scaffold with ABCB5+ stem cells and maintaining the scaffold under conditions such that tissue is formed. In some embodiments the method of tissue engineering is a method for tissue regeneration and the scaffold is maintained under conditions such that tissue is regenerated. In yet other embodiments the method of tissue regeneration is a method for treating aged skin.

A method for tissue engineering by seeding a biological tissue scaffold with ABCB5+ stem cells and maintaining the scaffold under conditions such that tissue is formed is provided in other aspects of the invention.

The biological tissue scaffold may be, for instance, an allograft or autograft, a xenogeneic tissue and/or decellularized tissue.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

Several methods are disclosed herein of administering to a subject a composition for treatment of a particular condition. It is to be understood that in each such aspect of the invention, the invention specifically includes, also, the composition for use in the treatment of that particular condition, as well as use of the composition for the manufacture of a medicament for the treatment of that particular condition.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
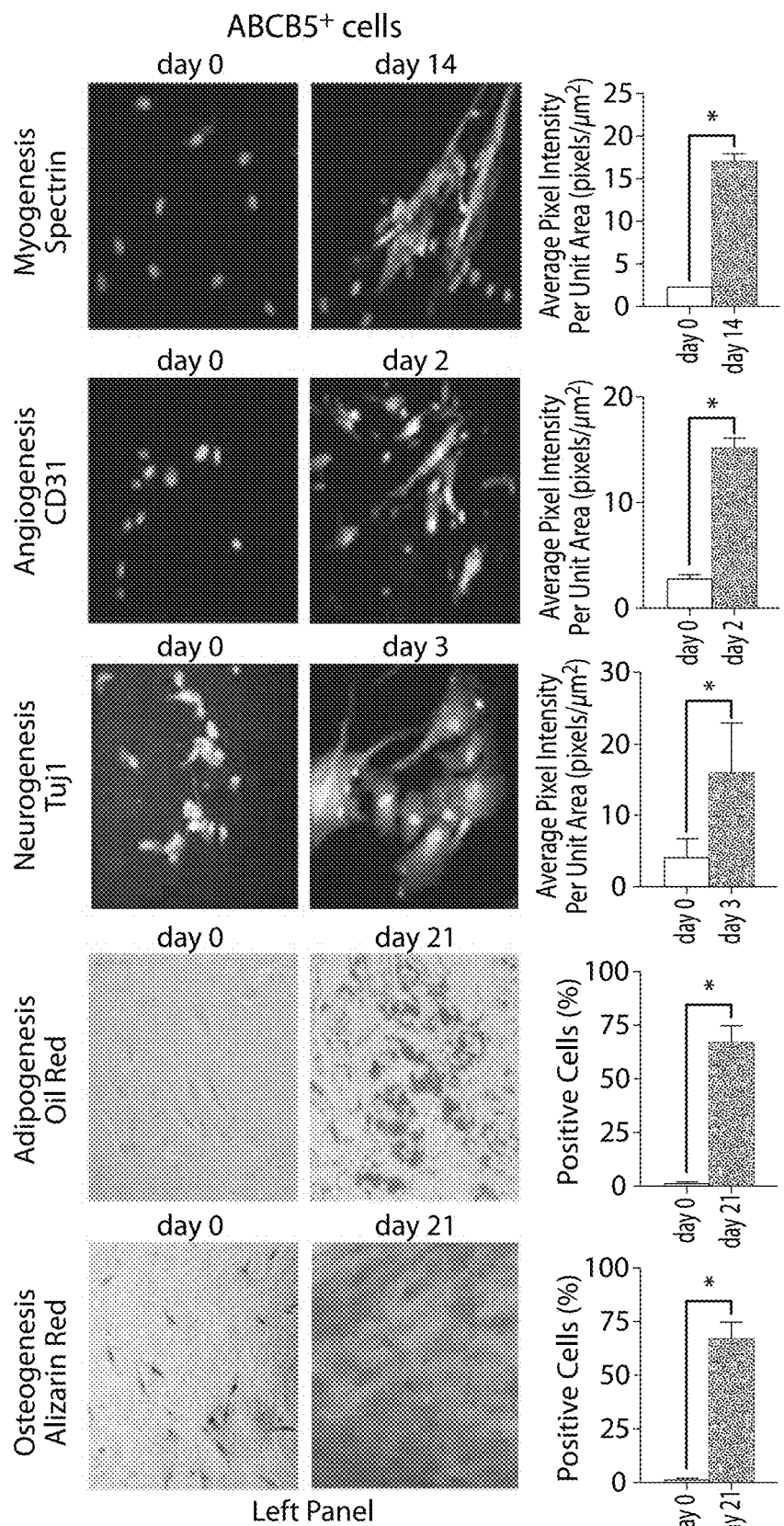
FIG. 1A-B. Multipotent differentiation potential of ABCB5+ cells. Immunofluorescence staining (top three rows) of ABCB5+(left panel) or ABCB5− (right panel) human skin cells for expression of spectrin (myogenesis assay), CD31 (angiogenesis assay), and TUJ1 (neurogenesis assay), before and after differentiation. Nuclei are visualized with DAPI. Bottom two rows: Oil Red (adipogenesis assay) and Alizarin Red (osteogenesis assay) staining of ABCB5+ (left panel) or ABCB5− (right panel) of human skin cells before and after differentiation. Aggregate analysis of pixel intensity for each marker (in myogenesis, angiogenesis and neurogenesis assays), or percent positively staining cells (in adipogenesis and osteogenesis assays), in replicate specimens (n=3) are shown in bar diagrams on the right. *, $P<0.05$.

The present invention is based in part upon the discovery that collagen glycosaminoglycan scaffolds seeded with ABCB5 positive stem cells demonstrate enhanced wound healing and tissue engineering properties. The constructs of the invention have been shown to possess unique regenerative activity that leads to tissue synthesis. Enhanced tissue synthesis is useful in repair and generation of tissues and wound repair and healing.

The cells useful according to the invention are ABCB5 positive stem cells. ABCB5 is a novel and important marker for the isolation of multipotent stem cell populations from normal human tissue. "ABCB5(+) stem cells," as used herein, refers to cells having the capacity to self-renew and to differentiate into mature cells of multiple adult cell lineages. These cells are characterized by the expression of ABCB5 on the cell surface. In some embodiments of the invention, ABCB5(+) stem cells are dermal or ocular stem cells.

"ABCB5 positive dermal mesenchymal stem cells" as used herein refers to cells of the skin having the capacity to self-renew and to differentiate into mature cells of multiple adult cell lineages such as bone, fat and cartilage. These cells are characterized by the expression of ABCB5 on the cell surface. In culture, mesenchymal stem cells may be guided to differentiate into bone, fat, cartilage, or muscle cells using specific media. (Hirschi K K and, Goodell M A. *Gene Ther.* 2002; 9: 648-652. Pittenger M F, et al., *Science.* 1999; 284: 143-147. Schwartz R E, et al., J Clin Invest. 2002; 109: 1291-1302. Hirschi K and Goodell M. *Differentiation.* 2001; 68: 186-192.)

The ABCB5 positive dermal mesenchymal stem cells can be obtained from skin. The skin may be derived from any subject having skin, but in some embodiments is preferably human skin. The skin may be derived from a subject of any age but in some embodiments is preferably adult skin, rather than adolescent or infant skin.

In other embodiments of the invention, ABCB5(+) stem cells are retinal stem cells. ABCB5(+) stem cells may be obtained from (e.g., isolated from or derived from) the basal limbal epithelium of the eye or from the retinal pigment epithelium (RPE). In some embodiments, ABCB5(+) stem cells are obtained from human eye. Other ABCB5(+) stem cell types such as, for example, those obtained from the central cornea may be used in various aspects and embodiments of the invention.

The ABCB5(+) stem cells may be isolated. An "isolated ABCB5(+) stem cell," as used herein, refers to a cell that has been removed from an organism in which it was originally found, or a descendant of such a cell. An isolated cell also refers to a cell that is placed into conditions other than the natural environment. Such a cell may later be introduced into a second organism or re-introduced into the organism from which it (or the cell or population of cells from which it descended) was isolated. Such a cell, once manipulated according to the methods of the invention is still considered to be an isolated cell. The term "isolated" does not preclude the later use of the cell thereafter in combinations or mixtures with other cells or in an in vivo environment.

ABCB5(+) stem cells may be obtained from a subject by isolating a sample of tissue, including skin cells, such as dermal cells, and ocular cells of the basal limbal epithelium or RPE, and then purifying the ABCB5(+) stem cells. It will be apparent to those of ordinary skill in the art that a sample can be enriched for ABCB5+ stems cells in a number of ways. For example, stems cells can be selected for using antibodies or other binding molecules that bind to ABCB5 cell surface molecules on the cells. Stem cells may be obtained directly from a donor or retrieved from cryopreservative storage. The stems cells may, for instance, be isolated using antibodies against ABCB5 and maintained in culture using standard methodology or frozen, e.g., in liquid nitrogen, for later use.

Specifically pure ABCB5+ dermal cell populations with mesenchymal stem cell molecular phenotype can be isolated from surgical specimens of healthy human skin using an established, sensitive and specific, ABCB5 monoclonal antibody (mAb) for example. The isolated ABCB5+ dermal stem cells have multipotent differentiation capacity such that they differentiate into cell lineages of all three germ layers, i.e. ectoderm, mesoderm and endoderm.

The present invention contemplates any suitable method of employing ABCB5-binding molecules such as, for example, monoclonal antibodies, polyclonal antibodies, human antibodies, chimeric antibodies, humanized antibodies, single-chain antibodies, F(ab')2, Fab, Fd, Fv or single-chain Fv fragments to separate ABCB5(+) stem cells from a mixed population of cells. Accordingly, methods include a method of producing a population of ABCB5(+) stem cells comprising the steps of providing a cell suspension of cells; contacting the cell suspension with a monoclonal antibody, or a combination of monoclonal antibodies, which recognize(s) an epitope, including ABCB5, on the ABCB5 (+) cells; and separating and recovering from the cell suspension the cells bound by the monoclonal antibodies. The monoclonal antibodies may be linked to a solid-phase and utilized to capture ABCB5+ stem cells. The bound cells may then be separated from the solid phase by known methods depending on the nature of the antibody and solid phase.

"Monoclonal antibody," as used herein, refers to an antibody obtained from a single clonal population of immunoglobulins that bind to the same epitope of an antigen. Monoclonal based systems appropriate for preparing cell populations of the invention include magnetic bead/paramagnetic particle column utilizing antibodies for either positive or negative selection; separation based on biotin or streptavidin affinity; and high speed flow cytometric sorting of immunofluorescent-stained LSCs mixed in a suspension of other cells. Thus, the methods of the present invention include the isolation of a population of cells and enhancement using monoclonal antibodies raised against surface antigen ABCB5 (e.g., monoclonal antibodies that selectively bind ABCB5). In some instances, commercially available antibodies or antibody fragments that selectively bind ABCB5 may be used in the methods disclosed herein. Such antibodies are considered to selectively bind to ABCB5 if they bind or are capable of binding to ABCB5 with a greater affinity that the affinity with which the monoclonal antibodies may bind to other antigens (i.e., antigens other than ABCB5). Such binding may be measured or determined by standard protein-protein interaction assays (e.g., antibody-antigen or ligand-receptor assays) such as, for example, competitive assays, saturation assays or standard immunoassays including, without limitation, enzyme-linked immunosorbent assays, radioimmunoassays and radio-immunofilter binding assays.

The ABCB5(+) stem cells may be prepared as substantially pure preparations. The term "substantially pure," as used herein, refers to a preparation that is substantially free of cells other than ABCB5(+) stem cells. For example, a substantially pure preparation of ABCB5(+) stem cells may constitute a preparation in which at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% percent of the total cells present in a preparation are ABCB5(+) stem cells.

The compositions of the invention comprise a substrate such as, for example, a biocompatible material that promotes wound healing, including biodegradable scaffolds. ABCB5 (+) stem cells may be added to the substrate or scaffold to form, for example, tissue or tissue grafts for transplantation. The scaffold is a highly porous lattice comprised of collagen and glycosaminoglycan, i.e. a collagen glycosaminoglycan matrix or scaffold. Examples of collagen glycosaminoglycan scaffolds include those listed in U.S. Pat. Nos. 4,060,081, 4,280,954 and 4,505,266. Other materials useful in the collagen glycosaminoglycan scaffolds include but are not limited to chondroitin 6-sulfate, chondroitin 4-sulfate, heparin, heparin sulfate, keratan sulfate, dermatan sulfate, chitin and chitosan. The collagen glycosaminoglycan scaffolds serves as a supporting or scaffolding structure into which blood vessels and surrounding tissue cells migrate from within a tissue cavity, a process referred to as "infiltration". Infiltration is responsible for creating a new tissue, which replaces the scaffold as it biodegrades.

In some embodiments the scaffold is INTEGRA®. INTEGRA® is an FDA approved acellular dermal skin substitute comprised of extracellular matrix (collagen and GAG). It has been used in the treatment of wide tissue defects or nonhealing wounds like venous leg ulcers.

"Compositions," herein, may refer to an isolated cell preparations or scaffolds, including tissue scaffolds and artificial scaffolds. The compositions of the invention, in some instances, are enriched with isolated ABCB5(+) stem cells. A composition is considered to be enriched with isolated ABCB5(+) stem cells if the ABCB5(+) stem cells are the predominant cell subtype present in the preparation. For example, an ABCB5(+) stem cell-enriched composition is a composition in which at least 50%, at least 55%, at least 60%, at least 65%, at least 70%, at least 75%, at least 80%, at least 85%, at least 90%, at least 95%, at least 98%, at least 99% or 100% of the cells of the composition are ABCB5(+) stem cells. In some embodiments, a composition enriched with isolated ABCB5(+) stem cells is one in which less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2% or less than 1% of the cells of the composition are ABCB5(−) cells. In some embodiments, the cells of a composition are only dermal cells. For instance, the scaffold is seeded with cells such that all the cells are ABCB5+ dermal cells. That is, in some embodiments, a composition may not contain non-dermal cells. In some embodiments the cells do not include keratinocytes and/or epidermal cells. In some embodiments, the cells of a composition are only ocular cells. That is, in some embodiments, a composition may not contain non-ocular cells. In some embodiments, a composition may not contain ABCB5(−) ocular cells.

The scaffolds of the present invention can be formatted in a variety of manners, such as a single sheet, or as a laminated sheet containing multiple layers or sheets of collagen. In certain embodiments, the scaffolds comprise 2-15 sheets. Such sheets can be held together by stitches or sutures.

In a particular embodiment, the polymer further comprises a bioactive molecule, for example, a small molecule or a peptide in addition to the stem cells. The bioactive molecule may be non-covalently incorporated into the polymer, for example, as a suspension, encapsulated as particles, microparticles, or colloids, or as a mixture thereof. The bioactive molecule may also be covalently incorporated into the polymer, using any suitable chemistry for attachment of the bioactive molecule to the polymer. The bioactive molecule can be any therapeutically desirable molecule, such as a growth factor, an anti-microbial, an analgesic, a hemostatic, a pro-angiogenic agent, or an anti-angiogenic agent. In exemplary embodiments, the polymer comprises one or more of FGF2, NGF, doxycycline, amoxicillin, and poly-L-lysine.

In another particular embodiment, the scaffolds have a width of at least 10 cm. For example, the scaffold can have a width of at least 10 cm and a length of at least 10 cm. Accordingly, certain scaffolds can have a surface area of more than 100 cm2, e.g., 4002. Scaffolds of the invention may have a biaxial strength of at least 80 N or more.

Tissue scaffolds of the invention can be used in multiple applications, including but not limited to covering a tissue deficit or wound, reinforcing tissue such as soft tissue, and organ/tissue generation or regeneration. Accordingly, in another aspect, the invention features a method for inducing repair of a damaged tissue, comprising contacting the damaged tissue with a scaffold of the invention. The invention further features a method for stimulating soft tissue regeneration, comprising contacting the soft tissue with an scaffold of the invention. When a scaffold is placed in contact with a tissue, the scaffold can increase proliferation of cells located near the scaffold. In addition, the scaffold can promote vascularization within a tissue to which it adheres. Accordingly, in another aspect, the invention provides a method of stimulating proliferation of cells in a tissue, comprising contacting the tissue with a scaffold such that cell proliferation is stimulated. The invention further provides a method of inducing vascularization of a tissue, comprising contacting the tissue with an scaffold such that vascularization occurs within the tissue.

The scaffold may be shaped to fill a tissue defect. In most cases this can be achieved by trimming the polymer fibers with scissors or a knife; alternatively, the scaffold can be cast from a polymer solution formed by heating or dissolution in a volatile solvent.

The mesenchymal stem cells are seeded onto the scaffold by application of a cell suspension to the scaffold. This can be accomplished by soaking the scaffold in a cell culture container, or injection or other direct application of the cells to the scaffold.

The scaffold seeded with cells is implanted at the site of the defect using standard surgical techniques. The scaffold can be seeded and cultured in vitro prior to implantation, seeded and immediately implanted, or implanted and then seeded with cells. In an embodiment, cells are seeded onto and into the scaffold and cultured in vitro for between approximately sixteen hours and two weeks, although it can be longer. Cell density at the time of seeding or implantation will vary under the circumstances. For example, cell density may be approximately 25,000 cells/mm$^3$. The skilled artisan will know the appropriate cell density.

As used herein, a subject may be a mammal such as, for example, a human, non-human primate, cow, horse, pig, sheep, goat, dog, cat or rodent. Human ABCB5(+) stem cells and human subjects are particularly important embodiments.

In some embodiments, the isolated ABCB5(+) stem cells (e.g., as a composition in the form of an ABCB5(+) stem cell graft or as a preparation of cells delivered to an implanted graft) may be administered to a subject more than once. Thus, in some embodiments, a subject may be administered multiple doses or grafts (e.g., 2, 3, 4 or more) of isolated ABCB5(+) stem cells over the course of several weeks, months or years. In some embodiments, the stem cells are administered again 3 months, 6 months, 9 months, 12 months, 18 months, 21 months or 24 months after the first application. The number of applications and frequency of application may depend, for example, on the degree of cellular regeneration achieved after the first stem cell administration/transplantation. The number and frequency of stem cell applications may be determined by a medical professional (e.g., surgeon, physician).

The compositions of the invention (scaffold seeded with ABCXB5+ stem cells) are useful in wound healing. Most wounds in skin and other organ systems are characterized by a loss of cells and connective tissue matrix from the protective outer layer as well as the underlying layers and tissues. In the case of skin wounds, the epidermis is the outer layer that is lost. The epidermis overlies the dermis as well as deeper structures such as fat, muscle and bone. Closure of large wounds in skin and other organ systems typically requires the production of billions of cells, nutrition through a vascular network and mechanical strength from proteins and glycosaminoglycans present in a nascent extracellular matrix (ECM).

The term "wound," for purposes herein, refers broadly to an injury to an organ or organ system. In the case of the skin, the injury may be to the epidermis, the dermis and/or the subcutaneous tissue. Skin wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include burn wounds, pressure sores, venous stasis ulcers, and diabetic ulcers. The term "deep wound" includes both Grade III and Grade IV wounds. The methods of the invention are useful for treating all grades of wounds, including chronic and acute wounds. The term "chronic wound" refers to a wound that has not healed within 30 days.

The term "promoting wound healing," for purposes herein, refers to enabling reconstitution of the normal physiologic barrier of an organ or organ system. In the case of skin wounds, promoting wound healing may include the induction of the formation of granulation tissue, and/or the induction of wound contraction, and/or the induction of revascularization, and/or the induction of epithelialization (i.e., the generation of new cells in the epithelium). In some embodiments, the ABCB5+ cells may function at least in part by the secretion of mediators, such as, for instance, VEGF.

The types of wounds to be treated by the methods of the invention include various kinds of wounds including, but are not limited to: surgical wounds; traumatic wounds; radiation injury wounds; toxic epidermal necrolysis wounds; infectious wounds; neoplastic wounds; full-thickness wounds; partial-thickness wounds; and burn wounds, as well as wounds arising from various types of ulcers, such as skin ulcers, corneal ulcers, arterial obstructive ulcers, continuous pressure-induced decubital and diabetic ulcers, burn ulcers, injury ulcers, radiation ulcers, drug-induced ulcers, post-operative ulcers, inflammatory ulcers, ulcers of the gastrointestinal tract, simple ulcers and other types of angiopathic ulcers, and chronic (intractable) ulcers.

The methods of various embodiments of the invention may be particularly useful in treating complex wounds or difficult-to-heal wounds. Many factors can adversely affect the wound healing process, including infection, radiated tissue, systemic illness, medications, patient age, patient health, and the nutritional status of the subject. In addition, any process that impedes peripheral blood circulation, such as arteriosclerosis, prolonged pressure, varicose vein disease, and venous stasis, can adversely affect the delivery of oxygen, nutrients, chemical signals, and appropriate cell types to mediate healing in an injured subject, will impair wound healing. Factors which inhibit wound healing include wound desiccation, medication, such as chemotherapy or steroids, and poor patient health and/or nutrition. Certain partial and full thickness injuries, such as burns, skin grafts, and various types of ulcers, resist repair and produce significant pain and discomfort for the subject.

The general physical condition of the patient is also important in wound healing. As age increases, the ability to repair injured tissue decreases as the skin becomes thinner and the number of fibroblasts and amount of total skin collagen decrease. Disease states such as alcoholism, anemia, diabetes, malnutrition, shock, and uremia lead to impaired oxygen and nutrient delivery to the wound site, thereby inhibiting the healing process. Also, diseases leading to monocytopenia can significantly impair wound healing.

Medications used to treat disorders can produce impaired wound healing. Chemotherapy, used to eliminate dividing cells in cancer patients, also suppresses the ability of such a patient to heal wounds, which is also dependent upon new cell growth. Steroids negatively impact all three phases of wound repair, inhibiting the initial inflammatory response, slowing the production of new epithelium and vascular tissue, and weakening the collagen matrix in the scar tissue.

Bacterial wound infection is a common local cause for prolonged wound healing. Human skin is typically colonized by a number of microorganisms, including *Candida albicans, Staphylococcus epidermidis, Staphylococcus aureus*, and some *Streptococcus* strains. Thus, any wound which exposes underlying tissues to the environment becomes infected with at least resident microbial flora. Wounds which are well tended and in highly vascularized tissue resist infection, while those in ischemic tissue are much more susceptible to infection.

In some embodiments the subject may have a skin wound. In other embodiments the subject may have an ocular condition such as an ocular wound (e.g., dead, damaged or infected ocular cells) in, for example, the corneal epithelium. Thus, the corneal epithelium may be wounded in a subject having an ocular condition in accordance with the invention.

In some embodiments the scaffold of the invention may be combined with a device for exerting pressure on a wound. Cells within the wound can be subjected to a controlled strain using devices that mechanically induce tension or compression in a steady or time-dependent manner as necessary. To apply controlled, localized forces to a wound surface a device having a number of microchannels fluidically connected to microstructures, such as microchambers for example, within a matrix that can be positioned on a wound surface may be used. Vacuum pressure (or positive pressure) applied to each microchamber is controlled via the microchannels. The term "vacuum pressure," for purposes herein, refers to a pressure in a chamber or material of interest that is lower in magnitude than of a reference chamber, material, tissue, or atmosphere. The term "positive pressure", for purposes herein, refers to a pressure in a chamber or material of interest that is higher in magnitude than that of a reference chamber, material, tissue, or atmosphere. The term "pressure", for purposes herein, is intended to encompass both vacuum pressure and positive pressure. The scaffold of the invention may be applied to the wound before, after, or intermittently with a device for applying pressure.

Wound healing involves fibrin clot formation, recruitment of inflammatory cells, re-epithelialization, and matrix formation and remodeling. Immediately after tissue injury, blood vessel disruption leads to the extravasation of blood and concomitant platelet aggregation and blood coagulation resulting in fibrin clot formation. Activated platelets trapped within the fibrin clot degranulate and release a variety of cytokines and growth hormones. These cytokines and growth hormones help to recruit inflammatory cells to the site of injury, to stimulate angiogenesis, and to initiate the tissue movements associated with re-epithelialization and connective tissue contraction.

Neutrophils and monocytes are recruited to the site of injury by a number of chemotactic signals including the growth factors and cytokines released by the degranulating platelets, formyl methionyl peptides cleaved from bacterial proteins, and the by-products of proteolysis of fibrin and other matrix proteins. Neutrophil infiltration ceases after a few days, but macrophages continue to accumulate by continued recruitment of monocytes to the wound site. Activated macrophages release growth factors and cytokines thereby amplifying the earlier signals from the degranulating platelets. Exogenous factors can be applied to the wound to aid in these processes.

Thus, embodiments of the invention also include methods which involve the inclusion of soluble factors with ABCB5+ cells. Following placement of the device on the wound, the soluble factors added to the device (e.g., growth factors like epidermal growth factor, cytokines, PGDF, insulin like growth factor, TGF-beta, keratinocyte growth factor cytokine, TNF, chemokines, chemotactic peptides, tissue inhibitors of metalloproteinases, etc.) pass into the tissue.

It has been noted that a number of recombinant growth factors may accelerate the wound healing process, in both acute and chronic wounds, in animal models. These recombinant derived factors include Platelet-Derived Growth Factor (PDGF), Fibroblast Growth Factor (FGF), Epidermal Growth Factor (EGF), and Transforming Growth Factors α and β (TGF-α and TGF-β). Additionally, other recombinant growth factors, including insulin, Insulin-like Growth Factors I and II (IGF-I and IGF-II, respectively), Interferons (IFNs), Interleukins (ILs), KGF (Keratinocyte Growth Factor), Macrophage Colony Stimulating Factor (M-CSF), Platelet-Derived Endothelial Cell Growth Factor (PD-ECGF), and Stem Cell Factor (SCF), may promote the activation, proliferation, and/or stimulation of cell types involved in the wound healing process.

The soluble factors may be proteins or may be expressed in cells. Protein, peptide, or polypeptide refers to a polymer of amino acids, and these terms are used interchangeably. The polymer may include natural or unnatural amino acids. The protein or polypeptide may be produced in vitro or in vivo via natural, recombinant, synthetic, or other means. The protein or polypeptide may have post-translational modifications or may have been modified chemically to include phosphorylation, glycosylation, farnesylation, acetylation, methylation, oxidation of thiols, etc.

Another use for the compositions of the invention is in tissue regeneration. Wound healing can be achieved through either tissue repair or tissue regeneration. In comparison to repair, which usually results in a formation of a scar, tissue regeneration provides complete morphological and functional restoration of normal structures. Spontaneous tissue regeneration does not happen in postnatal life; however, it can be at least partially aided by exogenous biological matrices, such as the scaffolds, clinically known as INTEGRA® (Integra LifeSciences, Plainsboro, N.J.), which have been approved by the U.S. Food and Drug Administration for use in massively burned patients and for the treatment of reconstructive defects and chronic wounds. The regenerated skin is mechanically competent, fully vascularized, and sensitive to touch and heat or cold[6], but is lacking critical skin appendages, e.g., hair follicles and sweat glands[5].

Transplantation of grafts containing ABCB5-positive stem cells, but not ABCB5-deficient dermal grafts, will further enhance INTEGRA®-induced regenerative wound healing and potentially enhance skin appendages formation by virtue of increased local availability of regenerative response-associated, multipotent stem cell populations. Significant improvements of the wound healing response are hereby anticipated to be accompanied by simultaneous regeneration of dermis and epidermis and decreased scar formation.

In this aspect of the invention, the scaffolds seeded with ABCB5 positive cells are used to generate tissue by induction of differentiation. Isolated and purified mesenchymal stem cells can be grown in an undifferentiated state through mitotic expansion in a specific medium. These cells can then be harvested and activated to differentiate into bone, cartilage, and various other types of connective tissue by a number of factors, including mechanical, cellular, and biochemical stimuli. Human mesenchymal stem cells possess the potential to differentiate into cells such as osteoblasts and chondrocytes, which produce a wide variety of mesenchymal tissue cells, as well as tendon, ligament and dermis, and this potential is retained after isolation and for several population expansions in culture. Thus, by being able to isolate, purify, greatly multiply, and then activate mesenchymal stem cells to differentiate into the specific types of mesenchymal cells desired, such as skeletal and connective tissues such as bone, cartilage, tendon, ligament, muscle, and adipose, a process exists for treating skeletal and other connective tissue disorders. The term connective tissue is used herein to include the tissues of the body that support the specialized elements, and includes bone, cartilage, ligament, tendon, stroma, muscle and adipose tissue.

In another aspect, the present invention relates to a method for repairing connective tissue damage. The method comprises the steps of applying the scaffolds to an area of connective tissue damage under conditions suitable for differentiating the stem cells into the type of connective tissue necessary for repair.

The term "connective tissue defects" refers to defects that include any damage or irregularity compared to normal connective tissue which may occur due to trauma, disease, age, birth defect, surgical intervention, etc. Connective tissue defects also refers to non-damaged areas in which bone formation is solely desired, for example, for cosmetic augmentation.

The scaffolds are also useful in the treatment of liver disease. Liver disease includes disease such as hepatitis which result in damage to liver tissue. More generally, the scaffolds of the present invention can be used for the treatment of hepatic diseases, disorders or conditions including but not limited to: alcoholic liver disease, hepatitis (A, B, C, D, etc.), focal liver lesions, primary hepatocellular carcinoma, large cystic lesions of the liver, focal nodular hyperplasia granulomatous liver disease, hepatic granulomas, hemochromatosis such as hereditary hemochromatosis, iron overload syndromes, acute fatty liver, hyperemesis gravidarum, intercurrent liver disease during pregnancy, intrahepatic cholestasis, liver failure, fulminant hepatic failure, jaundice or asymptomatic hyperbilirubinemia, injury to hepatocytes, Crigler-Najjar syndrome, Wilson's disease, alpha-1-antitrypsin deficiency, Gilbert's syndrome, hyperbilirubinemia, nonalcoholic steatohepatitis, porphyrias, non-cirrhotic portal hypertension, noncirrhotic portal hypertension, portal fibrosis, schistosomiasis, primary biliary cirrhosis, Budd-Chiari syndrom, hepatic veno-occlusive disease following bone marrow transplantation, etc.

In some embodiments, the invention is directed to treating a neurodegenerative disease, with the scaffolds of the invention. In some cases, the invention contemplates the treatment of subjects having neurodegenerative disease, or an injury to nerve cells which may lead to neuro-degeneration. Neuronal cells are predominantly categorized based on their local/regional synaptic connections (e.g., local circuit interneurons vs. longrange projection neurons) and receptor sets, and associated second messenger systems. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, proprioceptive neurons (in the trigeminal mesencephalic nucleus), ciliary ganglion neurons (in the parasympathetic nervous system), etc. A person of ordinary skill in the art will be able to easily identify neuronal cells and distinguish them from non-neuronal cells such as glial cells, typically utilizing cell-morphological characteristics, expression of cell-specific markers, secretion of certain molecules, etc. "Neurodegenerative disorder" or "neurodegenerative disease" is defined herein as a disorder in which progressive loss of neurons occurs either in the peripheral nervous system or in the central nervous system. These disorders include injury related neuronal damage such as spinal cord injury and head injury.

Most of the chronic neurodegenerative diseases are typified by onset during the middle adult years and lead to rapid degeneration of specific subsets of neurons within the neural system, ultimately resulting in premature death. Compositions comprising dermal mesenchymal stem cells may be administered to a subject to treat neurodegenerative disease alone or in combination with the administration of other therapeutic compounds for the treatment or prevention of these disorders or diseases.

The utility of adult stem cells in the treatment of neurodegenerative disease has been described. It has been demonstrated that mesenchymal stem cells can change into neuron-like cells in mice that have experienced strokes. Journal of Cell Transplantation Vol. 12, pp. 201-213, 2003. Additionally, stem cells derived from bone marrow developed into neural cells that hold promise to treat patients with Parkinson's disease, amyotrophic lateral sclerosis (ALS), and spinal cord injuries.

The methods of the invention are also useful in the treatment of disorders associated with kidney disease. Mesenchymal stem cells previously injected into kidneys have been demonstrated to result in an almost immediate improvement in kidney function and cell renewal. Resnick, Mayer, Stem Cells Brings Fast Direct Improvement, Without Differentiation, in Acute Renal Failure, EurekAlert!, Aug. 15, 2005. Thus, the scaffolds of the invention may be administered to a subject having kidney disease alone or in combination with other therapeutics or procedures, such as dialysis, to improve kidney function and cell renewal.

Other diseases which may be treated according to the methods of the invention include diseases of the cornea and lung. Therapies based on the administration of mesenchymal stem cells in these tissues have demonstrated positive results. For instance, human mesenchymal stem cells have been used to reconstruct damaged corneas. Ma Y et al, Stem Cells, Aug. 18, 2005. Additionally stem cells derived from bone marrow were found to be important for lung repair and protection against lung injury. Rojas, Mauricio, et al., American Journal of Respiratory Cell and Molecular Biology, Vol. 33, pp. 145-152, May 12, 2005. Thus the dermal mesenchymal stem cells of the invention may also be used in the repair of corneal tissue or lung tissue.

The ABCB5(+) stem cells may be autologous to the subject (obtained from the same subject) or non-autologous such as cells that are allogeneic or syngeneic to the subject. Alternatively, the ABCB5(+) stem cells may be obtained from a source that is xenogeneic to the subject.

Allogeneic refers to cells that are genetically different although belonging to or obtained from the same species as the subject. Thus, an allogeneic human ABCB5(+) stem cell is a stem cell obtained from a human other than the intended recipient of the stem cells. Syngeneic refers to cells that are genetically identical or closely related and immunologically compatible to the subject (i.e., from individuals or tissues that have identical genotypes). Xenogeneic refers to cells derived from or obtained from an organism of a different species than the subject.

The ABCB5(+) stem cells in accordance with the invention may be expanded ex-vivo or in vitro prior to the application to the scaffold or in vivo after administration. Thus, in some instances, ABCB5 expression provides a basis for identifying, isolating, cloning, propagating, and expanding ABCB5(+) stem cells in vitro. Any suitable method of employing agents, e.g., isolated peptides, e.g., antibodies, that bind to ABCB5 to separate ABCB5(+) stem cells from other cells may be used. The isolated ABCB5(+) stem cells may be maintained in an appropriate culture environment using, for example, a combination of media, supplements and reagents. Optionally, feeder cell populations or conditioned media obtained from feeder cell populations may be used to expand the ABCB5(+) stem cell populations.

Adhesion, attachment and matrix factors that may be used for stem cell expansion in accordance with the invention include, without limitation, E-cadherin, collagen, fibronectin, superfibronectin, heparin sulfate proteoglycan, ICAM-I, laminin, osteopontin, proteoglycan, E-selectin, L-selectin, VCAM and vitronectin.

Bioactives and supplements that may be used for stem cell expansion in accordance with the invention include, without limitation, enzymes (e.g., cathepsin G, Flt-3/Fc), proteins and peptides (e.g., activin A, albumin, angiogenin, angiopoietin, BAX inhibiting peptide, heregulin beta-1, SMAC/Diablo), vitamins, hormones and various other substances (e.g., L-ascorbic acid, dexamethasone, EGF, EGF-receptor, embryonic fluid (bovine), flt3-ligand, progesterone, retinoic acid, retinyl acetate, thrombopoietin and TPO), antibodies, chemokines, cytokines, growth factors and receptors.

Culture reagents that may be used for stem cell expansion in accordance with the invention include, without limitation, antibiotics (e.g., cycloheximide, etoposide, gentamicin, mitomycin, penicillin-streptomycin), classical media (e.g., Claycomb Medium, Dulbecco's Modified Eagle Medium, Iscove's Modified Dulbecco's Medium, Minimum Essential Medium), cell freezing medium-DMSO, Claycomb Medium without L-glutamine, Stemline® Medium (Sigma-Aldrich, USA).

Compositions of the present invention may comprise stem cells, or an isolated preparation of stem cells, the stem cells characterized by the expression of ABCB5 on their cell surface cografted with a glycosaminoglycan scaffold. A composition may comprise a preparation enriched with isolated ABCB5(+) stem cells, or it may comprise a substantially pure population of ABCB5(+) stem cells. Compositions are meant to encompass scaffolds, discussed herein.

The compositions, in some embodiments, may comprises additional bioactives and supplements to promote cell regeneration and differentiation. Such bioactives and supplements that may be used in accordance with the invention are describe above and include, without limitation, various enzymes, proteins and peptides, vitamins, antibodies, chemokines, cytokines, growth factors and receptors. In some embodiments, the compositions may comprise an immunosuppressant and/or an anti-vasculogenesis agent. For example, in some embodiments, a composition may comprise cyclosporin (e.g., CyA), which may be used to prevent and/or treat graft rejections. In some embodiments, the compositions may comprise bevacizumab (e.g., AVASTIN®). The use of anti-vasculogenesis agent may be used, in some instances, to prevent blood vessel formation, which often occurs after transplantation and may lead to graft rejection. In some embodiments, an immunosuppressant and/or an anti-vasculogenesis agent is not administered as a component of a composition or scaffold, but rather is administered independently prior to or subsequent to administration of ABCB5(+) stem cells.

The ABCB5+ cells may be genetically or recombinately engineered. Recombinant can refer to organisms, cells, nucleic acids, and proteins. Recombinant cells and organisms are cells and organisms containing recombinant DNA. Recombinant DNA refers to a nucleic acid sequence which is not normally found in nature. Usually this term refers to two or more pieces of DNA spliced together to form an unnatural product. Recombinant protein is protein produced from recombinant DNA (i.e., a nucleic acid which differs from that which occurs in nature). In producing a recombinant protein, the regulatory sequences of the gene encoding the protein are usually different than the ones that occur in the natural gene. The gene also may have been placed in an organism which normally does not possess the gene in order to produce that protein in the desired organism.

The insertion of desired genes or other nucleic acid constructs into cells seeded onto the scaffold can be accomplished using routine genetic and recombinant engineering techniques, e.g., as described in Ausubel et al., eds., 1989, Current Protocols in Molecular Biology, Green Publishing Associates, Inc. and John Wiley & Sons, Inc., New York.

The dermal mesenchymal stem cells may be modified to express proteins which are also useful in the therapeutic indications, as described in more detail herein. For example, the cells may include a nucleic acid that produces at least one bioactive factor which further induces or accelerates the differentiation of the mesenchymal stem cells into a differentiated lineage and/or the cells may include a nucleic acid that produces a secreted mediator. In the instance that bone is being formed, the bioactive factor may be a member of the TGF-beta superfamily comprising various tissue growth factors, particularly bone morphogenic proteins, such as at least one selected from the group consisting of BMP-2, BMP-3, BMP-4, BMP-6 and BMP-7. In other instances the secreted mediator may be VEGF.

Various techniques may be employed for introducing nucleic acids into cells. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid according to the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake.

One method of introducing exogenous genetic material into the dermal mesenchymal stem cells is by transducing the cells using replication-deficient retroviruses. Replication-deficient retroviruses are capable of directing synthesis of all virion proteins, but are incapable of making infectious particles. Accordingly, these genetically altered retroviral vectors have general utility for high-efficiency transduction of genes in cultured cells. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in the art.

The major advantage of using retroviruses is that the viruses insert efficiently a single copy of the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types. The major disadvantages of using a retrovirus expression vector are (1) insertional mutagenesis, i.e., the insertion of the therapeutic gene into an undesirable position in the target cell genome which, for example, leads to unregulated cell growth and (2) the need for target cell proliferation in order for the therapeutic gene carried by the vector to be integrated into the target genome. Despite these apparent limitations, delivery of a therapeutically effective amount of a therapeutic agent via a retrovirus can be efficacious if the efficiency of transduction is high and/or the number of target cells available for transduction is high.

Yet another viral candidate useful as an expression vector for transformation of dermal mesenchymal stem cells is the adenovirus, a double-stranded DNA virus Like the retrovirus, the adenovirus genome is adaptable for use as an expression vector for gene transduction, i.e., by removing the genetic information that controls production of the virus itself. Because the adenovirus functions usually in an extra-chromosomal fashion, the recombinant adenovirus does not have the theoretical problem of insertional mutagenesis. On the other hand, adenoviral transformation of a target dermal mesenchymal stem cell may not result in stable transduction. However, more recently it has been reported that certain adenoviral sequences confer intrachromosomal integration specificity to carrier sequences, and thus result in a stable transduction of the exogenous genetic material.

Thus, as will be apparent to one of ordinary skill in the art, a variety of suitable vectors are available for transferring exogenous genetic material into dermal mesenchymal stem cells. The selection of an appropriate vector to deliver a therapeutic agent for a particular condition amenable to gene replacement therapy and the optimization of the conditions for insertion of the selected expression vector into the cell, are within the scope of one of ordinary skill in the art without the need for undue experimentation.

Thus, the present invention makes it possible to genetically engineer dermal mesenchymal stem cells in such a manner that they produce polypeptides, hormones and proteins not normally produced in human stem cells in biologically significant amounts or produced in small amounts but in situations in which overproduction would lead to a therapeutic benefit. These products would then be secreted into the bloodstream or other areas of the body, such as the central nervous system. The human stem cells formed in this way and embedded in a scaffold can serve as a continuous drug delivery systems to replace present regimens, which require periodic administration (by ingestion, injection, depot infusion etc.) of the needed substance. This invention has applicability in providing hormones, enzymes and drugs to humans, in need of such substances. It is particularly valuable in providing such substances, such as hormones (e.g., parathyroid hormone, insulin), which are needed in sustained doses for extended periods of time and are associated with the tissue being repaired.

The ABCB5(+) stem cells may be isolated to produce totipotent, multipotent or pluripotent stem cells (e.g., induced pluripotent stem cells (iPSCs)), from which other cells, tissues and/or whole animals can develop. Thus, methods for directly reprogramming, or inducing, ABCB5(+) stem cells to become totipotent, multipotent or pluripotent stem cells before or after the cells are seeded in the scaffold, are provided in some aspects of the invention. The term "reprogramming," as used herein, refers to a process that reverses the developmental potential of a cell or population of cells (e.g., an ABCB5(+) stem cell). Thus, reprogramming refers to a process of driving a cell to a state with higher developmental potential, i.e., backwards to a less differentiated state. The cell to be reprogrammed can be either partially or terminally differentiated prior to reprogramming. In some embodiments, reprogramming encompasses a complete or partial reversion of the differentiation state, i.e., an increase in the developmental potential of a cell, to that of a cell having a totipotent, multipotent or pluripotent state. In some embodiments, reprogramming encompasses driving an ABCB5(+) stem cell to a totipotent, multipotent or pluripotent state, such that the cell has the developmental potential of an embryonic stem cell, i.e., an embryonic stem cell phenotype. Reprogramming also encompasses partial reversion of the differentiation state of a cell to a state that renders the cell more susceptible to complete reprogramming to a totipotent, multipotent or pluripotent state when subjected to additional manipulations.

Totipotent, multipotent or pluripotent stem cells may be generated from ABCB5(+) stem cells (referred to herein as "reprogrammed ABCB5(+) cells") using several reprogramming factors. The resultant cells, which have a greater developmental potential than the ABCB5(+) stem cells, may then become the source of stem cells for further manipulations. A "reprogramming factor" as used herein, refers to a developmental potential altering factor, the expression of which contributes to the reprogramming of a cell, e.g., an ABCB5(+) stem cell, to a less differentiated or undifferentiated state, e.g., to a cell of a pluripotent state or partially pluripotent state. Reprogramming factors include OCT4, SOX2, KLF 4 and c-MYC (otherwise known as the "Yamanaka factors"). Other reprogramming factors include, without limitation, SOX 1, SOX 3, SOX15, SOX 18, NANOG, KLF1, KLF 2, KLF 5, NR5A2, LIN28, 1-MYC, n-MYC, REM2, TBX3, TERT and LIN28. Any combination of two or more of the foregoing transcription factors may be used to reprogram isolated ABCB5(+) stem cells. Methods of reprogramming cells to a totipotent, multipotent or pluripotent state are described by Stadtfeld and Hochedlinger [33], incorporated herein by reference in its entirety.

Differentiated cells may also be produced and incorporated into the scaffold from reprogrammed ABCB5(+) cells. The methods may comprise expressing in the reprogrammed ABCB5(+) cells any one or more differentiation factors necessary to promote differentiation into a more mature, differentiated cell type such as, for example, a blood cell, platelet, stromal cell, bone cell, muscle cell, skin cell, fat cell or neural cell. As used herein, the term "differentiation factor" refers to a developmental potential altering factor such as a protein, or small molecule that induces a cell to differentiate to a desired cell-type, e.g., a differentiation factor reduces the developmental potential of a cell. Differentiation to a specific cell type may involve simultaneous and/or successive expression of more than one differentiation factor. The methods may further comprise growing the reprogrammed ABCB5(+) cells under conditions for promoting differentiation to form a differentiated cell.

A "stem cell" as used herein is an undifferentiated or partially differentiated cell that has the ability to self-renew and has the developmental potential to differentiate into multiple cell types. A "pluripotent cell" is a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve). A "multipotent" cell is a cell that has the developmental potential to differentiate into cells of one or more germ layers, but not all three. These cells include, for instance, adult stem cells, such as for example, hematopoietic stem cells and neural stem cells. A "totipotent" cell is a cell that has the developmental potential to differentiate into all the differentiated cells in an organism, including extra-embryonic tissues. Stem cells may have a propensity for a differentiated phenotype; however, these cells can be induced to reverse and re-express the stem cell phenotype. This process is referred to as "dedifferentiation" or "reprogramming."

The ACB5(+) stem cells, reprogrammed ABCB5(+) cells and differentiated cells of the invention can be manipulated under standard conditions for these cell types. The treatment of the cells may be performed before or after the cells are incorporated in to the scaffold and in vitro, ex vivo or in vivo. For instance, the cells may be present in the body or in a culture medium. The manipulations may be performed under high or low-oxygen conditions.

A "culture medium" contains nutrients that maintain cell viability and support proliferation. A typical culture medium includes: salts, buffers, amino acids, glucose or other sugar(s), antibiotics, serum or serum replacement, and/or other components such as peptide growth factors. Cell culture media for use in deriving and maintaining totipotent, multipotent and pluripotent cells are known in the art. Culture medium may also include cell specific growth factors, such as angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor-alpha, cytokine-induced neutrophil chemotactic factor 1, cytokine-induced neutrophil, chemotactic factor 2-alpha, cytokine-induced neutrophil chemotactic factor 2-beta, beta-endothelial cell growth factor, endothelia 1, epidermal growth factor, epithelial-derived neutrophil attractant, fibroblast growth factor 4, fibroblast growth factor 5, fibroblast growth factor 6 fibroblast growth factor 7, fibroblast growth factor 8, fibroblast growth factor b, fibroblast growth factor c, fibroblast growth factor 9, fibroblast growth factor 10, fibroblast growth factor acidic, fibroblast growth factor basic, glial cell line-derived neutrophil factor receptor-alpha-1, glial cell line-derived neutrophil factor receptor-alpha-2, growth related protein, growth related protein-alpha, growth related protein-beta, growth related protein-gamma, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-alpha, nerve growth factor, nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-alpha, platelet derived growth factor receptor-beta, pre-B cell growth stimulating factor, stem cell factor, stem cell factor receptor, transforming growth factor-alpha, transforming growth factor-beta, transforming growth factor-beta-1, transforming growth factor-beta-1-2, transforming growth factor-beta-2, transforming growth factor-beta-3, transforming growth factor-beta-5, latent transforming growth factor-beta-1, transforming growth factor-beta-binding protein I, transforming growth factor-beta-binding protein II, transforming growth factor-beta-binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The differentiation state of the cell can be assessed using any methods known in the art for making such assessments. For instance, the differentiation state of a cell treated according to the methods described herein may be compared with an untreated cell or cells treated with DNA using viral vectors to deliver DNA resulting in the expression of the same reprogramming or differentiation factors.

The dose of the stem cells may be defined by the number of cells included in the scaffold and varies within wide limits and will, of course be fitted to the individual requirements in each particular case. The number of cells used will depend on the weight and condition of the recipient and other variables known to those of skill in the art.

The present invention also provides any of the above-mentioned compositions in kits, optionally including instructions for use of the composition for the treatment of a condition described herein. That is, the kit can include a description of use of the composition for participation in any biological or chemical mechanism disclosed herein. The kits can further include a description of activity of the condition in treating the pathology, as opposed to the symptoms of the condition. That is, the kit can include a description of use of the compositions as discussed herein. The kit also can include instructions for use of a combination of cells and scaffold for treatment of the diseases. Instructions also may be provided for administering the composition by any suitable technique. The kits may also be one or more reagents associated with the isolation and purification of the dermal mesenchymal stem cells, i.e. ABCB5 antibodies, and instructions for isolating and/or purifying the cells.

The kits described herein may also contain one or more containers, which may contain the composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Multipotent Differentiation Plasticity of ABCB5+ Dermal Stem Cells In Vitro and In Vivo We have previously shown that ABCB5 identifies a mesenchymal stem cell population in human dermis, where it confers membrane hyperpolarization and determines as a regulator of membrane potential the propensity of skin progenitors to undergo differentiation. Additional studies have revealed that ABCB5 confers drug resistance and marks cancer stem cell (CSC) subsets with specific differentiation plasticity in human melanomas, where it also correlates with clinical disease progression.

We have shown that ABCB5+ skin cells reside in the reticular dermis and are distinct from neighboring mature fibroblasts, CD31+ endothelial cells, and CD34+ bulge cells. ABCB5 is expressed by 2.5-5% of all cells in human skin specimen. ABCB5+ cells co-expressed the mesenchymal stem cell markers CD29 (on 99.48±0.5% of cells), CD44 (99.09±0.9%), CD49e (92.61±4.0%), CD90 (100%), and CD166 (58.29±19.7%), as well as the stem cell marker CD133 (6.29±5.1%), but were negative for differentiation markers such as the endothelial lineage marker CD31, the hematopoietic lineage marker CD45, and the quiescent fibroblast marker CD34. Importantly, only distinct subpopulations of cells staining positively for the reported MSC markers (CD29, CD44, CD49e, CD90 and CD166) stained positively for ABCB5, whereas large proportions of cells expressing these antigens were found to be negative for ABCB5, demonstrating that ABCB5+ cells represent a unique novel subpopulation of mesenchymal stem cells.

We assessed multipotent differentiation plasticity of ABCB5+ dermal stem cells vis-à-vis ABCB5− cells in vitro and in vivo, in order to investigate whether ABCB5 represents a more specific marker for multipotent mesenchymal stem cells than currently available MSC antigens.

Figure 1B:
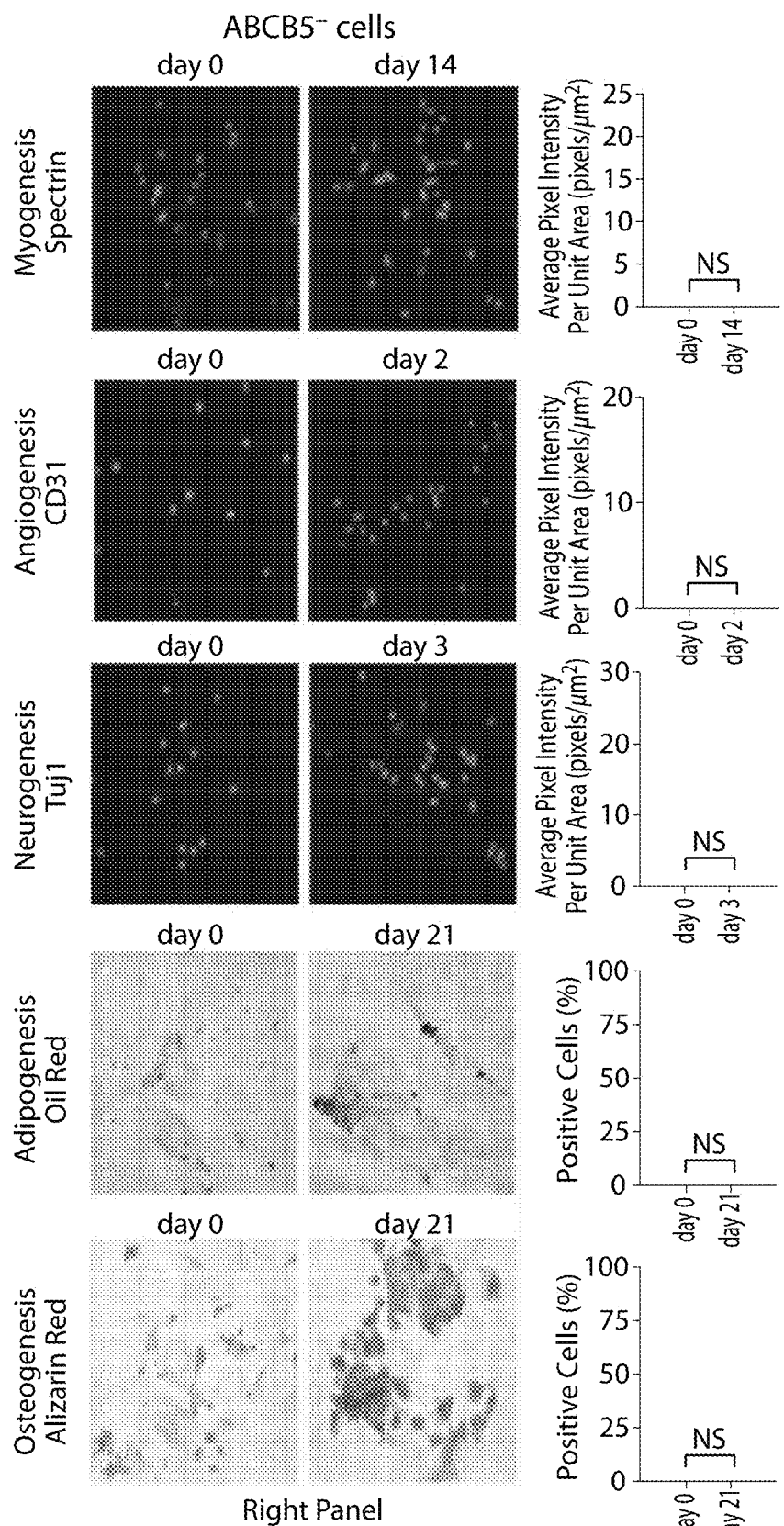

We examined the differentiation potential of ABCB5+ cells isolated by positive selection from dissociated skin cell suspensions derived from healthy human volunteers and compared it to the differentiation potential of ABCB5− dermal fibroblasts (FIG. 1). ABCB5+ or ABCB5− cells were cultured in neurogenic, angiogenic, myogenic, osteogenic or adipogenic lineage inducing media and their differentiation plasticity was assessed by measuring induction of RNA and protein expression of lineage-specific markers (i.e. spectrin—myogenesis, CD31—angiogenesis, TUJ1—neurogenesis, Oil Red—adipogenesis, and Alizarin Red—osteogenesis), as well as lineage-characteristic morphological changes (FIG. 1). Only ABCB5+, but not ABCB5− dermal cells were capable of giving rise to all three embryonic lineages (i.e. ectodermal (neurogenesis), mesodermal (myogenesis) and endodermal (angiogenesis) lineages) (FIG. 1).

To further dissect the differentiation plasticity of human ABCB5+ dermal MSC and to determine their niche-independent capacity for multipotent differentiation in vivo, we examined the in vivo myoregenerative potential of human ABCB5+ vs. ABCB5− skin-derived cells in an acute muscle injury model. ABCB5+ and ABCB5− skin cells were injected into cardiotoxin-injured tibialis anterior (TA) muscles of severely immunocompromised NOD/SCID/IL2Rγ−/− (NSG) mice. Representative immunofluorescence staining of murine muscles injected with human ABCB5+ and ABCB5− cells with human-specific β2-microglobulin, Δ-sarcoglycan and Spectrin were obtained. Nuclei are visualized with DAPI. Injected muscles and non-injected control muscles were harvested 2 weeks after transplantation and examined for expression of human-specific β2 microglobulin (β2M), which identifies all cells of human origin, and human-specific spectrin (SPTBN1) and delta-sarcoglycan (SGCD), which are specifically expressed by differentiated human but not murine myocytes. While immunostaining revealed the presence of β2M+ human cells in both ABCB5+ and ABCB5− cell-injected muscles, indicative of successful transplantation and engraftment, only TA muscles injected with ABCB5+ cells contained SPTBN1+ and SGCD+ differentiated myocytes. Real-time PCR analyses of injected and non-injected control muscles demonstrated expression of human-specific β2M transcripts in ABCB5+ and ABCB5− cell-injected muscles, but not in non-injected controls, and expression of human specific SPTBN1 and SGCD transcripts was demonstrated only in ABCB5+ cell-injected muscles. Thus, ABCB5 represents a highly specific marker for multipotent human dermal mesenchymal stem cells, with substantially enhanced discriminatory marker function over currently available MSC antigens. These findings highlight the ability of ABCB5+ dermal MSC as a novel cell source for stem cell-based tissue regeneration.

Example 2

Stem Cell Deficiency Phenotype of Abcb5 Knockout Mice

Figure 2:
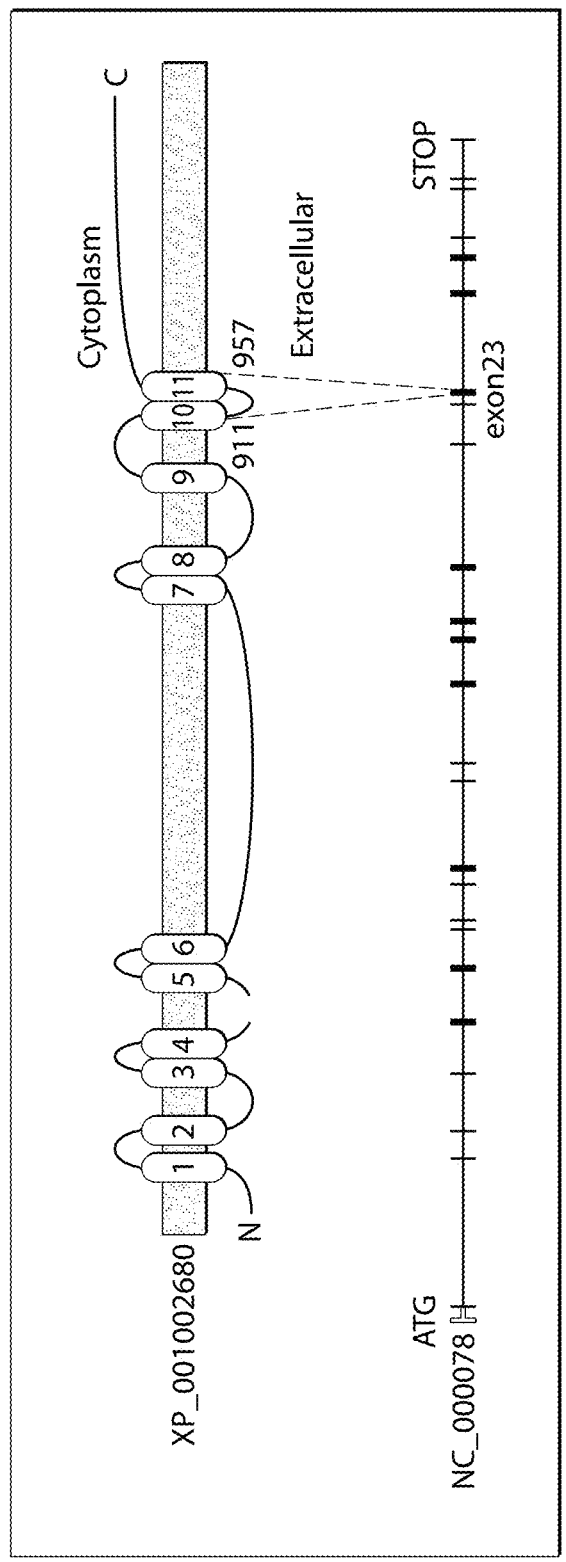
FIG. 2. Schematic of murine ABCB5 gene locus and protein topology. The murine Abcb5 gene contains 28 exons and spans 102 kb of genomic DNA at the 12qF2 locus. It encodes a 1255 AA protein with 11 transmembrane helices and 5 extracellular loops. Exon 23 encodes AA 911-957, which form an extracellular loop containing the 3C2-1D12 anti-ABCB5 antibody binding epitope.

In order to further dissect the role of ABCB5 in development and stem cell function, we created the first conditional Abcb5 knockout (KO) mouse. Until recently, ABCB5 protein function was studied extensively in *Homo sapiens*. The human ABCB5 gene encodes a 812 amino acid (AA) protein with five transmembrane helices flanked by both extracellular and intracellular ATP-binding domains[1]. Our previous studies revealed that one of our monoclonal anti-ABCB5 antibody clones, 3D2-1D12, which targets an extracellular loop containing amino acid residues 493-508 of the human ABCB5 protein, inhibits ABCB5-mediated Rhodamine-123 dye efflux, membrane polarization and doxorubicin transport[1,25], demonstrating critical functional importance of this extracellular loop region of the molecule. We have also previously cloned the corresponding ABCB5 mouse homologue, murine Abcb5[23]. A homologous part of the murine molecule was targeted in order to disrupt Abcb5 function in mice. Using the UCSC Blat search engine we identified that the mouse genomic region encoding the Abcb5 protein domain homologous to the 3C2-1D12 ABCB5 mAb-binding epitope is encoded by exon 23. Based on this finding a conditional KO construct where two loxP sites were inserted to flank the murine exon 23 was designed (FIG. 2).

Figure 3:
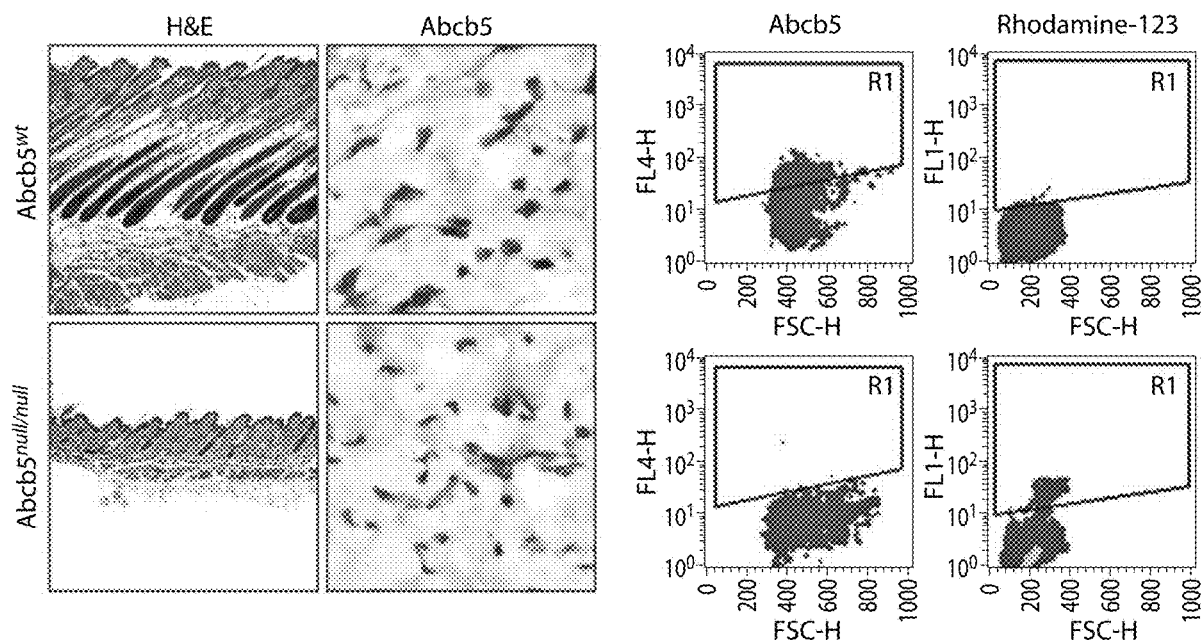
FIG. 3. Analysis of Abcb5 WT (upper panels) and Abcb5 KO (lower panels) mice. H&E staining shows thinning of the dermis with reduced subcutaneous fat and disorganized smooth musculature in KO animals (magnification same for WT and KO specimens). IHC and flow cytometry show complete loss of Abcb5 protein expression in Abcb5null/null mice. Rhodamine-123 efflux studies identify a de novo dye-retaining cell population in Abcb5null/null mice (R1 gate, right bottom panel), consistent with loss of a hallmark Abcb5 function, Rhodamine-123 efflux 1.

To determine the outcome of a complete loss of function, exon 23 of the Abcb5 gene was deleted using the Ella-Cre transgene, which expresses Cre recombinase in a mouse embryo at the zygote stage[48,49]. Deletion of the genomic region between the loxP sites was confirmed by PCR of genomic DNA. Heterozygous Abcb5null/WT mice were intercrossed to produce homozygous Abcb5null/null mutants, and loss of Abcb5 expression and function in Abcb5null/null mutants was confirmed by flow cytometric analyses and Rhodamine-123 efflux assays[1] (FIG. 3).

Relative quiescence is one of the distinguishing features attributed to various mammalian stem cell populations[50]. Skin stem cells were first identified as slow-cycling cells using so-called "pulse and chase" DNA labeling experimental approaches developed by Bickenbach[51], Morris[52] and Cotsarelis[50]. These approaches rely on incorporation of a labeled thymidine analog, uridine, into the nuclear DNA during the replication phase (S-phase) of the cell cycle. First, during the DNA labeling or "pulse" phase, cells or animals are exposed to the radioactively or chemically-labeled uridine (e.g. bromodeoxyuridine, BrdU), which is then incorporated into nuclear DNA during each cell division. Labeled uridine (e.g. BrdU) exposure is then withdrawn during the "chase" phase, with subsequent loss of the label by frequently dividing cells, over the course of approximately 48-72 hours. Slow-cycling cells, however, are capable of retaining the DNA label for prolonged periods of time; for example, bulge area stem cells of the mouse hair follicle can retain radioactively labeled uridine for at least 4 weeks[50], and are therefore termed "label-retaining cells"

Figure 4A:
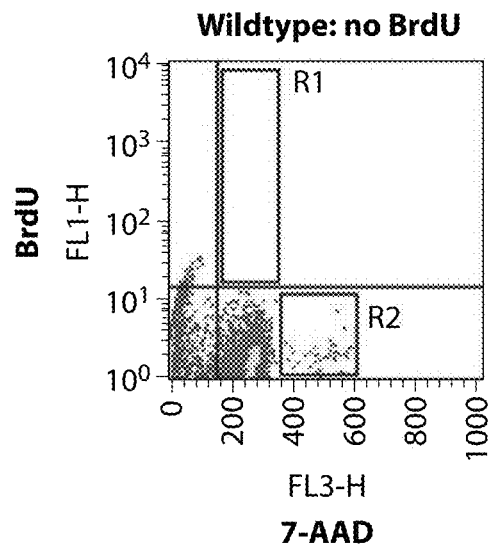
FIG. 4A-4C. Regulation of stem cell quiescence by ABCB5. Representative dual-color flow cytometric analyses of murine skin cells from Abcb5 WT (B) and Abcb5 KO (C) mice labeled with BrdU in vivo and from unlabeled Abcb5 WT controls (A). Cells are co-stained with anti-BrdU FITC antibody and 7-AAD. Brdu-positive cells in G0 phase of cell cycle are shown in the R1 gate. BrdU-negative cells in S/G2/M phases of the cell cycle are depicted in the R2 gate.
Figure 4B:
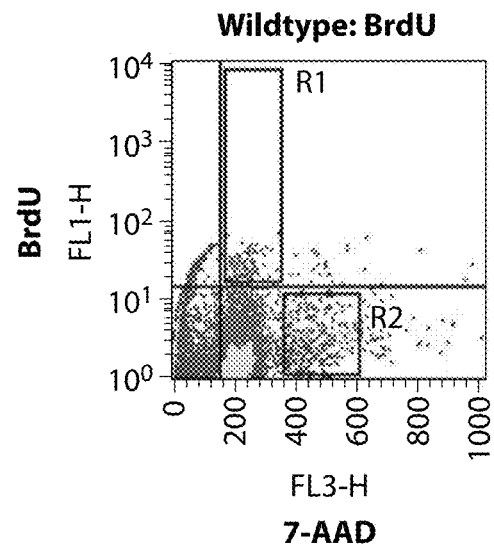
Figure 4C:
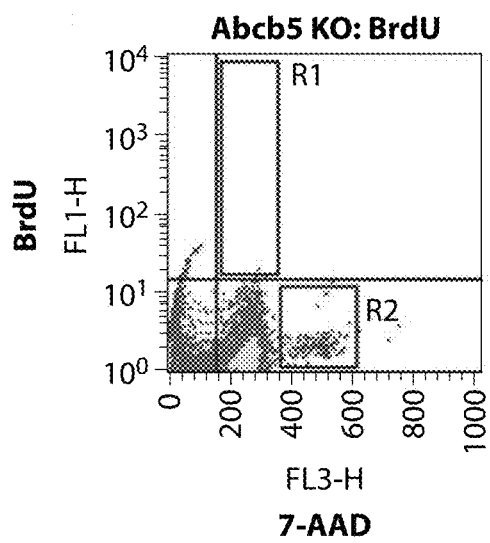

In order to determine whether ABCB5 identifies a quiescent label-retaining cell population in mammalian skin, consistent with the demonstrated stem cell phenotype, and whether intact ABCB5 function is required for the maintenance of stem cell quiescence, we performed in vivo BrdU-labeling experiments in Abcb5 WT and Abcb5 KO mice. Brdu is a non-radioactive uridine derivative, which can be detected using fluorescently-labeled anti-BrdU antibodies. Mice were subjected to a 9-day "pulse" of daily systemic (i.v.) BrdU administration designed to label slow-dividing cells, followed by a 4-week BrdU-free "chase" phase upon cessation of BrdU treatment. The percentage of BrdU-retaining cells in dissociated full thickness skin cell suspensions was then compared between Abcb5 WT and Abcb5 KO mice, using anti-BrdU antibody staining and flow cytometry. Cells were hereby co-stained with 7-amino-actinomycin D (7-AAD) dye, which binds to total DNA, for enumeration and characterization of cells with regard to their cell cycle position (FIG. 4). Flow cytometric analyses revealed that after a 4-week "chase", all Brdu-positive (i.e. label-retaining cells) in Abcb5 WT mice were found in the G0 phase (FIG. 4B, gate R1), and that this population was diminished by 74% in Abcb5 KO mice (FIG. 4C, gate R1). In addition, full thickness skin cell suspensions derived from Abcb5 KO mice exhibited 67% more proliferating BrdU-negative cells in the S/G2/M phase compared to those derived from Abcb5 WT mice (FIGS. 4B and 4C, gate R2), indicating that abrogation of normal ABCB5 function induces cellular proliferation of normally quiescent ABCB5+ cells.

Figure 5A:
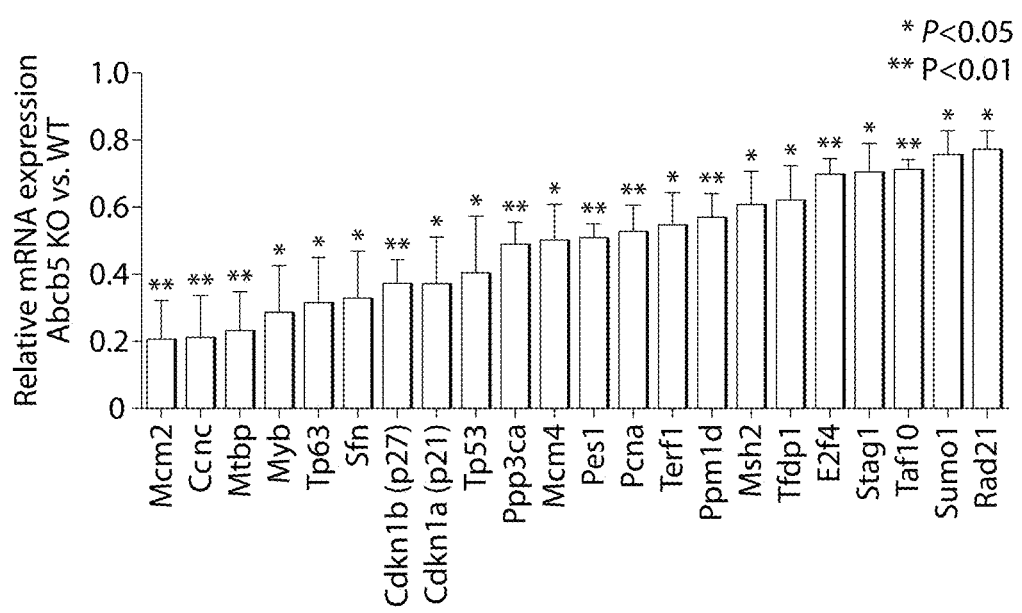
FIG. 5A-5B. Differential expression of genes involved in cell cycle regulation between Abcb5 KO mice Abcb5 WT mice. (A) A list of genes downregulated in Abcb5 KO versus Abcb5 WT mice as determined real-time PCR analyses. (B) Genes depicted here are downregulated in Abcb5 KO mice. Lines with arrows show known gene interactions. Gene relationships to canonical pathways such as p53 signaling, G1/S checkpoint regulation, cyclins and cell cycle regulation, and calcium signaling pathways, are annotated with lines without arrows. Gene relationships and interactions are based on Ingenuity Pathway Analysis (Ingenuity, Calif.).
Figure 5B:
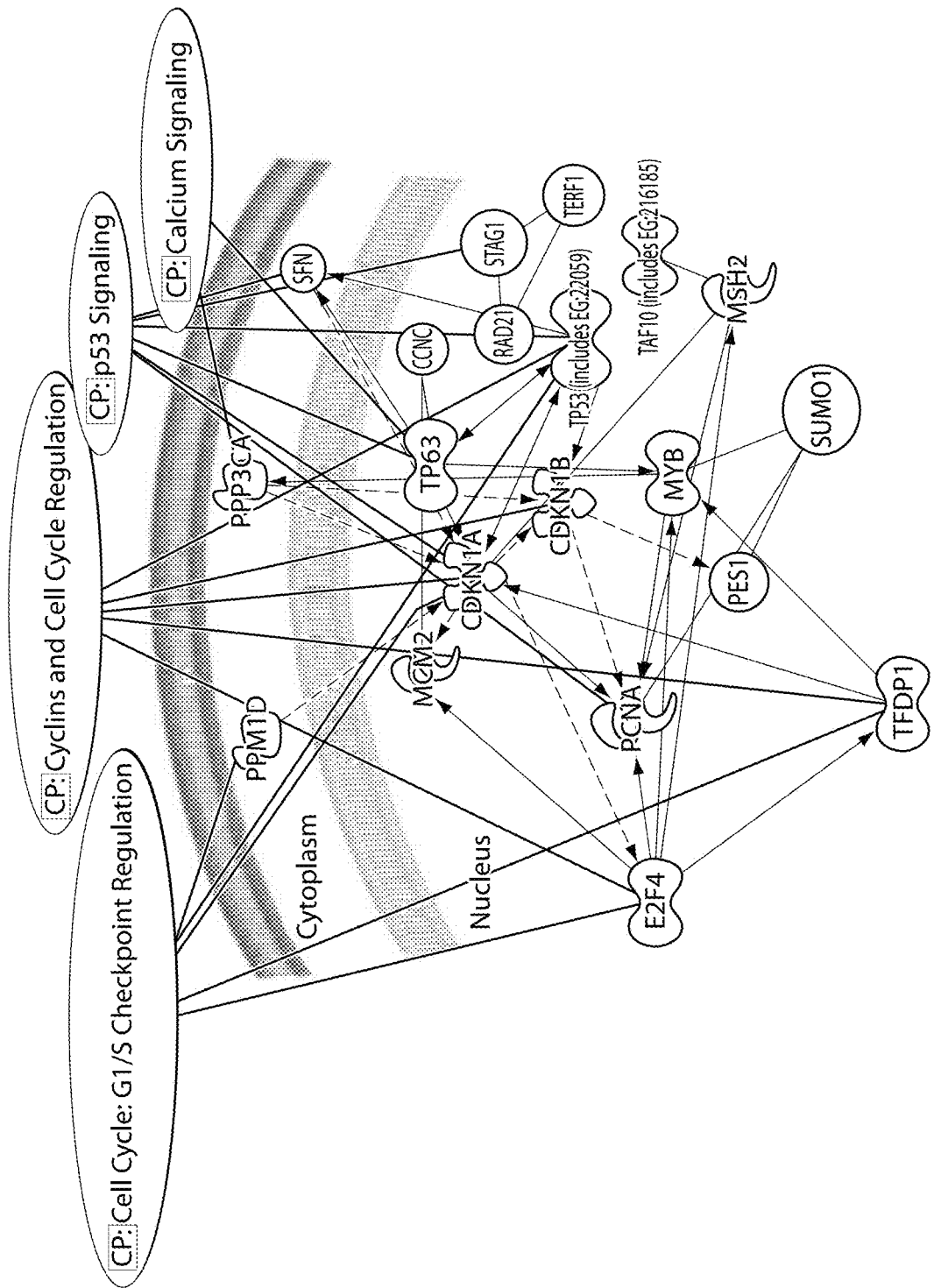

Consistent with this observation, real-time PCR analyses of 84 cell genes involved in cell cycle regulation (SABiosciences, catalog number PAMM-020), revealed a significant down-regulation in Abcb5 KO mice of 22 molecules involved in several canonical cell cycle pathways, including p53 signaling, G1/S checkpoint regulation, cyclins and cell cycle regulation, and calcium signaling pathways (FIG. 5) including, members of p53 family (p53 and p63) and cKip family (p21 and p27), which control G0/G1 cell cycle checkpoint and cellular quiescence.

These results indicate that ABCB5 regulates cell cycle progression and is required for the maintenance of stem cell quiescence. Abrogation of ABCB5 function leads to repression of critical negative regulators of G0/G1 cell cycle progression and to increased cellular proliferation. Withdrawal from cell cycle is a prerequisite for normal differentiation, and inability to do so may explain an impairment of normal wound healing in Abcb5 KO mice described below. The data further support the suitability of ABCB5 as a functionally relevant marker for stem cell isolation from mammalian skin.

Example 3

Impaired Wound Healing in Abcb5 Knockout Mice

Wound healing is a complex phenomenon, which progresses through four sequential phases: hemostasis, inflammation, proliferation, and remodeling with scar formation[53]. We investigated whether intact ABCB5 function is required for normal wound healing, utilizing Abcb5 WT and Abcb5 KO mice. Full-thickness cutaneous wounds were generated by removing 1 cm² of skin and panniculus, and mice were subsequently observed for 7 days during the early proliferative phase of wound healing. Wounds were photographed immediately after the surgical procedure and at the time of tissue harvest (day 7). Digital photographs captured at the end of the experiment were quantitatively analyzed in comparison to corresponding initial photographs by 2 independent observers blinded to the mouse genetic status.

Figure 6A:
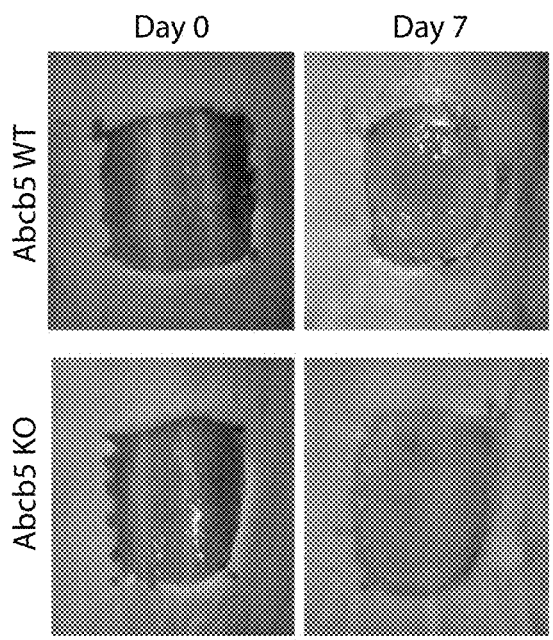
FIG. 6A-6C. Comparative wound healing analyses of Abcb5 KO and Abcb5 WT mice. (A) Representative day 0 and day 7 digital photographs of full thickness skin wounds generated in Abcb5 WT (top panel) and Abcb5 KO (bottom panel) mice. (B) Representative H&E staining of central wound cross-sections, surrounding skin and underlying muscle tissue harvested at experimental day 7 from Abcb5 WT (top panel) and Abcb5 KO (bottom panel) mice. (C) Quantitative analyses of wound closure (top panel) and inflammatory stroma thickness (bottom panel) of Abcb5 KO and Abcb5 WT wounds.
Figure 6B:
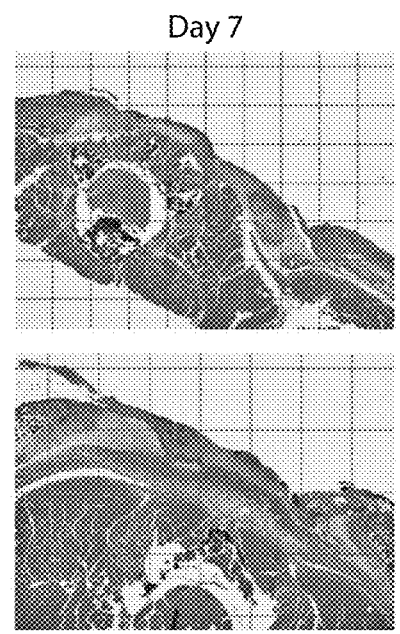
Figure 6C:
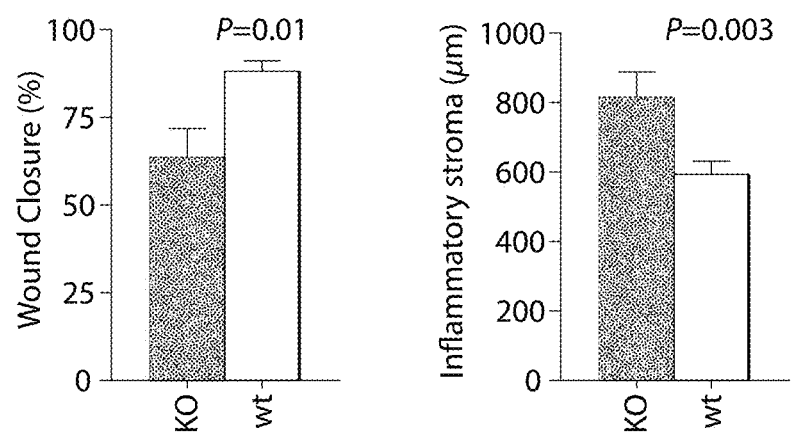

Wound closure was hereby calculated as a percentage of the original wound, based on measurements obtained by planimetric analyses as described previously[54], using the Image J software package (NIH, Bethesda, Md.). The data were compared using unpaired t tests with Welch's correction to account for unequal variances. Abcb5 KO mice (n=15) demonstrated significantly delayed wound closure in comparison to Abcb5 WT mice (n=19) (63.64±7.6% vs. 87.33±3.4%, mean±SEM, P=0.01) (FIG. 6). Additionally, inflammatory stroma thickness was measured in both groups on scanned, H&E-stained day 7 wound cross-sections using Aperio Image Scope software (Vista, Calif.), with Abcb5 KO wounds demonstrating significantly increased inflammatory stroma thickness in comparison to Abcb5 WT wounds (820.2±65.6 µm vs. 590.0±38.8 µm, mean±SEM, P=0.003) (FIG. 6).

Figure 7A:
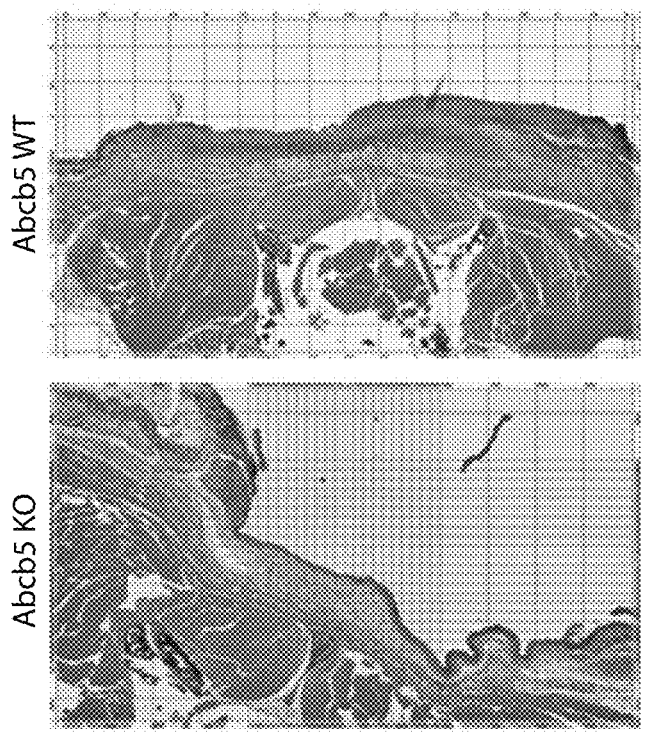
FIG. 7A-7C. Comparative CD31 expression analyses in Abcb5 KO and Abcb5 WT mice. (A) and (B), Representative H&E and CD31 staining of central wound cross-sections, surrounding skin and underlying muscle tissue harvested at experimental day 7 from Abcb5 WT (top panel) and Abcb5 KO (bottom panel) mice. (C) Quantitative analyses of vascular CD31+ layer thickness (top panel) and avascular CD31− layer thickness (bottom panel) in Abcb5 KO and Abcb5 WT wounds.
Figure 7B:
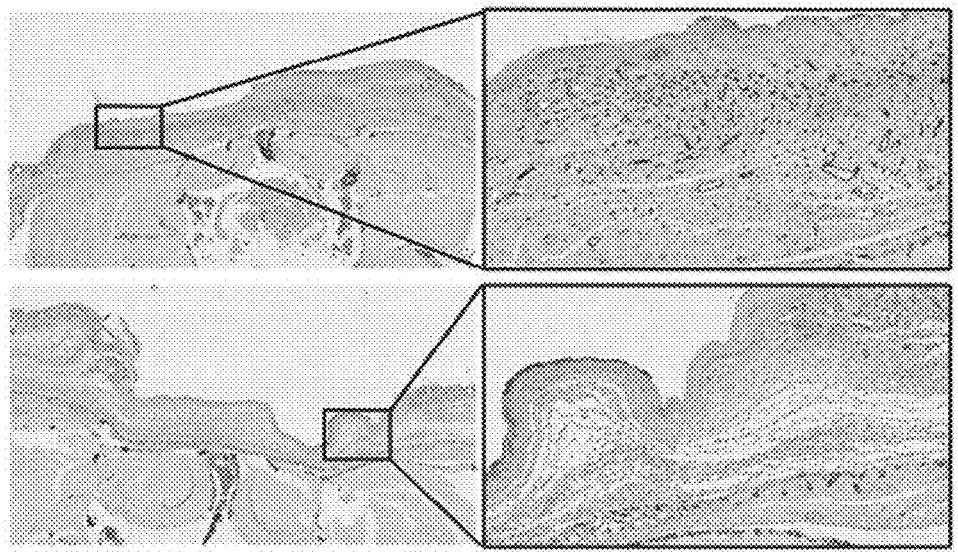
Figure 7C:
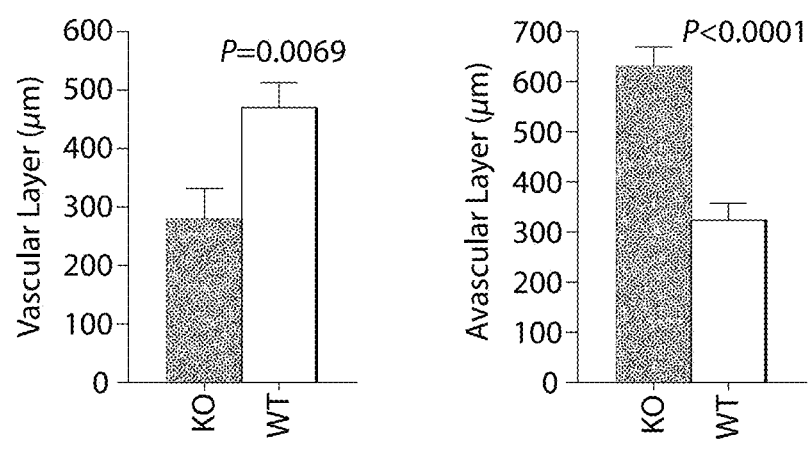

Neovascularization is one of the hallmarks of early stages of wound regeneration and is critical for control of hypoxia-induced excessive myofibroblast proliferation, which is thought to contribute to keloid scar formation (reviewed in[55]). Previous studies have shown that while wound angiogenesis is mainly achieved through sprouting of new vessels from pre-existing vessels, some of the newly formed vessels might originate from bone marrow progenitor cells[56]. Contribution of other resident stem cell populations to wound angiogenesis is unclear. Based on our previous observations of the critical role of ABCB5+ cells in human melanoma vasculogenesis[28], we hypothesized that intact ABCB5 function might also be essential for efficient angiogenesis in wounded skin. To test this hypothesis in additional preliminary studies generated since the last iteration of this proposal, vessel formation in murine skin wounds generated as described above was analyzed by comparing expression of the endothelial marker CD31 in Abcb5 KO and Abcb5 WT mice at day 7 after wounding in the context of the thickness of vascularized versus avascularized strata (layers) within the wound bed. Vascular CD31-positive and avascular CD31-negative layer thicknesses were measured in both groups on scanned, CD31-stained day 7 wound cross-sections using Aperio Image Scope software (Vista, Calif.), with Abcb5 KO wounds demonstrating significantly decreased vascular layer thickness (278.5±51.45 µm vs. 469.2±40.30 µm, mean±SEM, P=0.0069) and significantly increased avascular layer thickness (626.2±41.18 µm vs. 324.5±28.55 µm, mean±SEM, P<0.0001) compared to Abcb5 WT wounds (FIG. 7).

Figure 8:
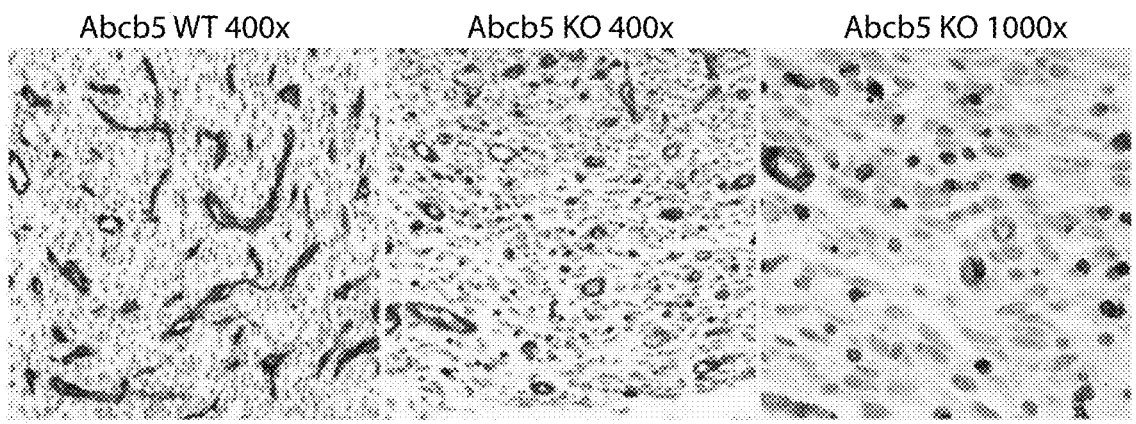
FIG. 8. Comparative analyses of vessel formation in Abcb5 KO and Abcb5 WT mice. Representative CD31 staining of vascular layers of central wound cross-sections from tissues harvested at experimental day 7 from Abcb5 WT (left panel) and Abcb5 KO (right panel) mice.

In contrast to wild type animals, where proliferating CD31-positive vessels formed variably elongated branching channels with well-formed lumens, similar areas from ABCB5 KO animals were focally either relatively devoid of CD31-positive structures, or were composed of occasional small vessel profiles admixed with solitary or small clusters of CD31-positive cells. These latter CD31-positive cells appeared to reflect inability to differentiate into tubules capable of the angiogenic sprouting necessary to form the arborizing network of mature vessels required for an efficient and productive healing response (FIG. 8).

Figure 9A:
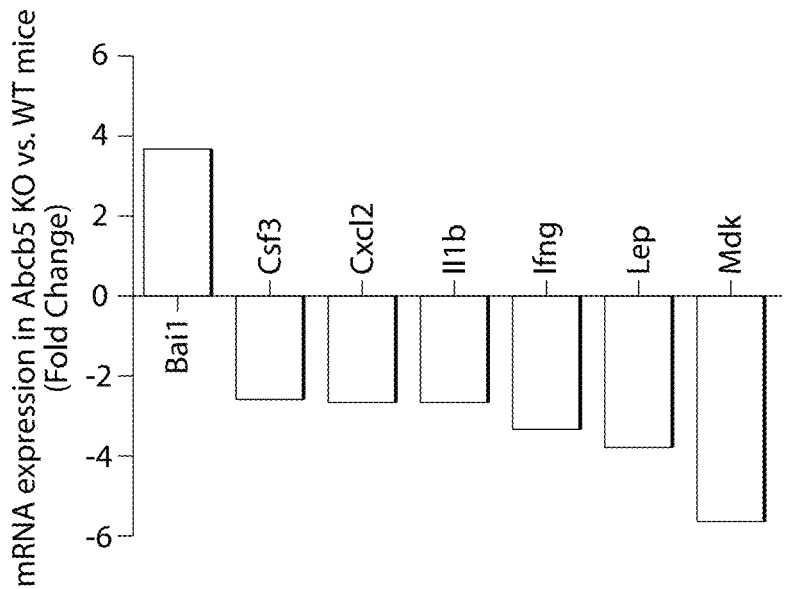
FIG. 9A-9B. Differential expression of genes involved in angiogenesis in Abcb5 KO vs. WT mouse wounds. (A) Gene expression levels as determined by real-time PCR analyses. (B) Pro-angiogenic cytokines down-regulated in Abcb5 KO wounds are shown and labeled. Arrows indicate pro-angiogenic effect. An anti-angiogenic transmembrane receptor, Bai1, which is over-expressed in Abcb5 KO wounds. The bar at the bottom indicates anti-angiogenic effect. Gene relationships are based on Ingenuity Pathway Analysis (Ingenuity, Calif.).
Figure 9B:
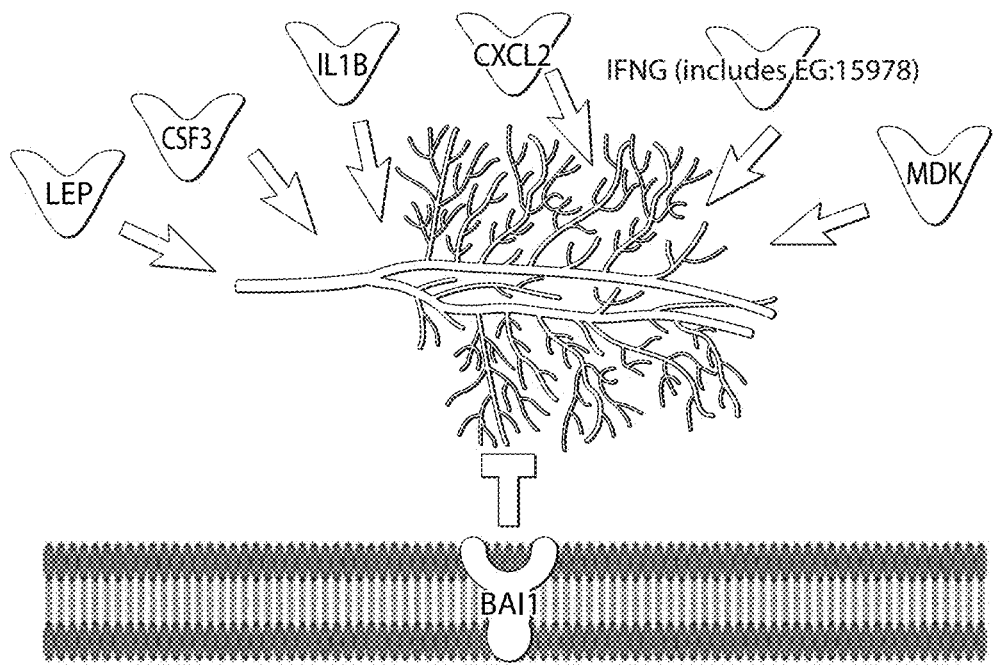

Consistent with this observation, real-time PCR analyses of 84 genes involved in angiogenesis (SABiosciences, catalog number PAMM-024Z), revealed significant down-regulation in Abcb5 KO wounds of pro-angiogenic cytokines, i.e. Csf3, CxC12, Il1b, Ifng, Lep, and Mdk and up-regulation of a known anti-angiogenic molecule, phosphatidylserine receptor Bai1 (FIG. 9), providing an initial explanation for highly inhibited and abnormal angiogenic pattern observed in Abcb5 KO wounds.

These results demonstrate impaired wound healing in Abcb5 KO mice characterized by delayed wound closure, increased inflammatory stroma thickness and aberrant angiogenesis, further supporting a critical functional role of ABCB5, and hence of ABCB5+ mesenchymal stem cells, in normal cutaneous wound healing.

Example 4

Effect of Human ABCB5+ Dermal MSC on Regenerative Wound Healing in NSG Mice

Figure 10A:
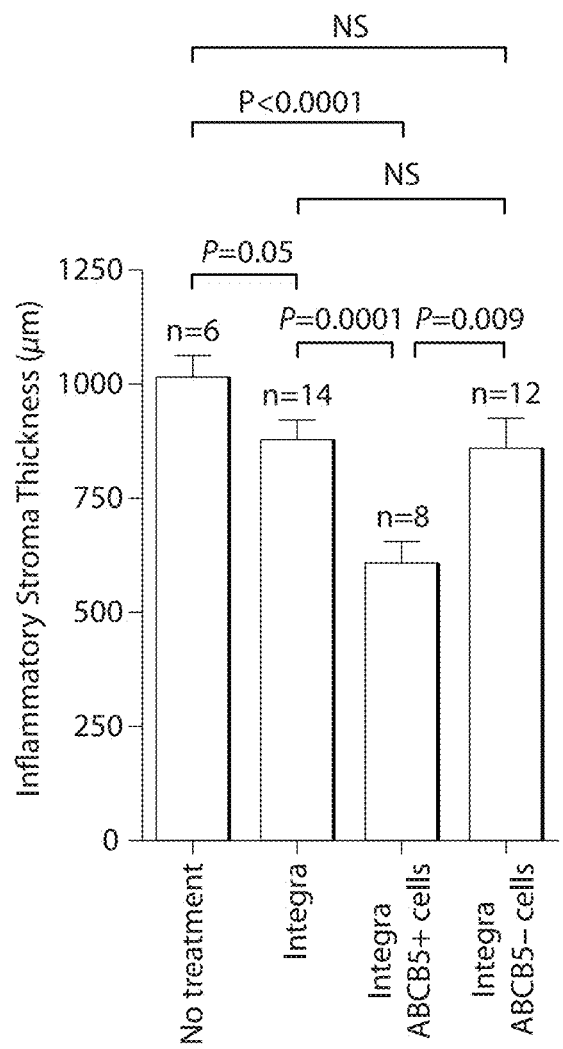
FIG. 10A-10D. Effect of ABCB5+ cells on wound healing in NSG mice. (A) Quantitative analyses of inflammatory stroma thickness of wounds inflicted in four experimental groups. (B) Representative H&E staining of wound cross-sections harvested at experimental day 14. (C) Detection of human cells injected into INTEGRA® matrices by human-specific β2M14 days after transplantation. Black arrows point to β2M+ human cell clusters and individual β2M+ human cells. (D) RT-PCR analyses of murine wound cross for expression of human-specific GAPDH, β2-microglobulin and murine ß-actin used as a loading control.
Figure 10B:
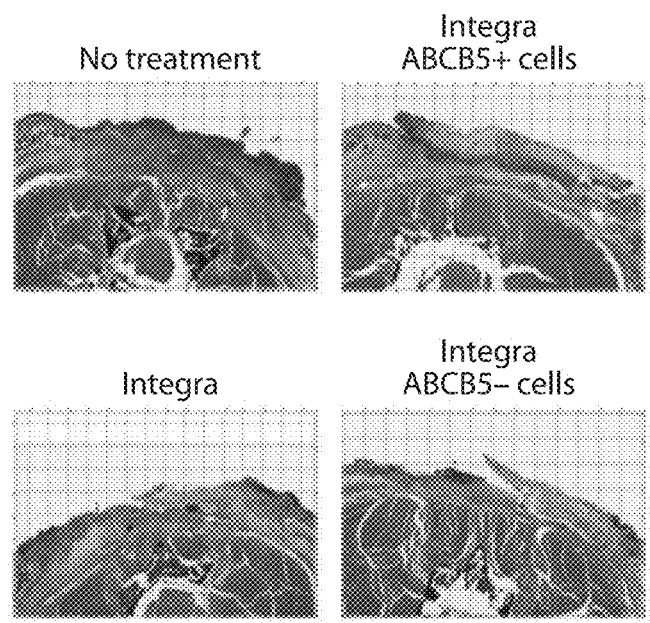
Figure 10C:
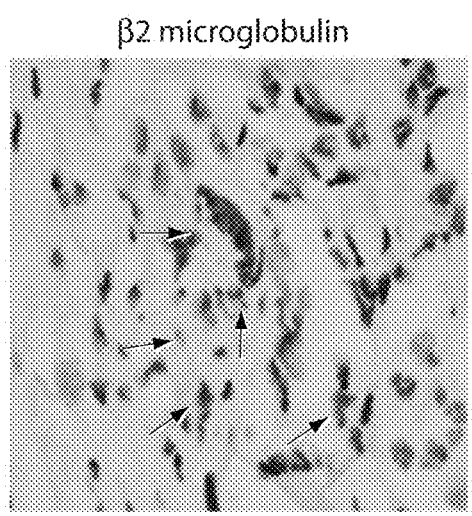
Figure 10D:
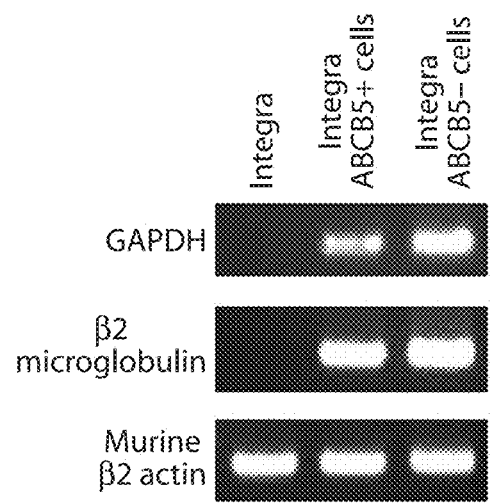

We investigated the effect of human ABCB5+ dermal MSC on wound healing in INTEGRA®-treated NSG mice using the following four treatment groups: (1) no treatment; (2) INTEGRA® only; (3) INTEGRA® injected with 1×10$^6$ ABCB5+ dermal MSC and (4) INTEGRA® injected with 1×10$^6$ ABCB5-positive dermal cells (FIG. 10B). Full-thickness cutaneous wounds were generated in all animals by removing 1 cm$^2$ of skin and panniculus as described in FIG. 6. Each wound in groups 2, 3 and 4 was immediately transplanted with 1 cm$^2$ INTEGRA® graft, followed by intra-INTEGRA® injection of either 1×10$^6$ ABCB5+ cells (group 3) or 1×10$^6$ ABCB5− cells (group 4). No cells were injected in experimental group 2. Group 1 served as a no treatment experimental control. At day 14 after the procedure, wound tissues, consisting of INTEGRA®, surrounding skin and underlying muscle tissue were harvested. Inflammatory stroma thickness was measured in all groups on scanned, H&E-stained day 14 wound cross-sections using Aperio Image Scope software (Vista, Calif.). Quantitative analyses revealed that mice treated with INTEGRA® and ABCB5+ human dermal MSC exhibited significantly decreased inflammatory stroma thickness compared to mice treated with INTEGRA® and ABCB5− dermal cells (608.0±46.7 µm vs. 855.4±69.8 µm, mean±SEM, P=0.009), mice treated with INTEGRA® alone (874.7±43.3 µm, P=0.0001), or untreated mice (1014±49.4 µm, P<0.0001). No difference was observed between mice treated with INTEGRA® alone and mice treated with INTEGRA® and ABCB5− dermal cells. Treatment with INTEGRA® only modestly decreased inflammatory stroma thickness compared to untreated wounds (FIG. 10A). To ensure viability of the human injected cell population, grafts were furthermore examined for expression of human-specific β2 microglobulin (β2M), an identifier of all cells of human origin. Immunostaining revealed the presence of β2M+ human cell clusters as well as individual β2M+ human cells (FIG. 10C) in cell-injected INTEGRA® grafts. Real-time PCR analyses of INTEGRA® grafts injected with either ABCB5+ or ABCB5-human dermal cells also demonstrated expression of human-specific GAPDH and β2M transcripts, which have not been detectable, as expected, in non-injected INTEGRA® only-treated controls (FIG. 10D). Thus, despite successful engraftment and persistence of viable ABCB5+ dermal MSC or viable ABCB5− dermal cells following injection into transplantable INTEGRA® matrices, only transplantation of ABCB5+ dermal MSC, but not ABCB5− human dermal cells further reduced inflammatory stroma thickness in wounded NSG mice, providing initial proof-of-principle for the specific therapeutic utility of this novel MSC population to further enhance regenerative wound healing.

Example 5

Humanized Mouse Model

Figure 11A:
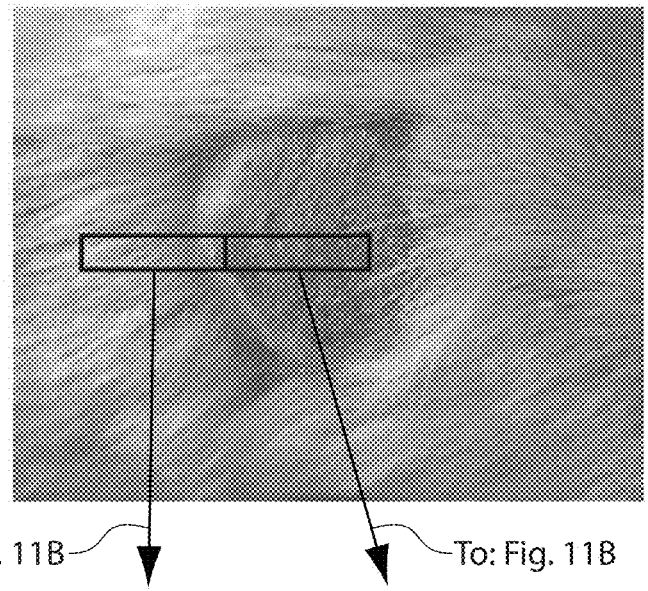
FIG. 11A-11C. Human to mouse xenograft model showing established human skin graft on mouse back 8 weeks post-engraftment (A). Corresponding histopathology demonstrating the human-murine skin anastomosis is shown in (B). Wounding of the human xenograft (C) enables imunohistochemical detection of specific dermal cells and extracellular matrix elements at timepoints 0, 2, 4, and 7 days post wounding (top to bottom).
Figure 11B:
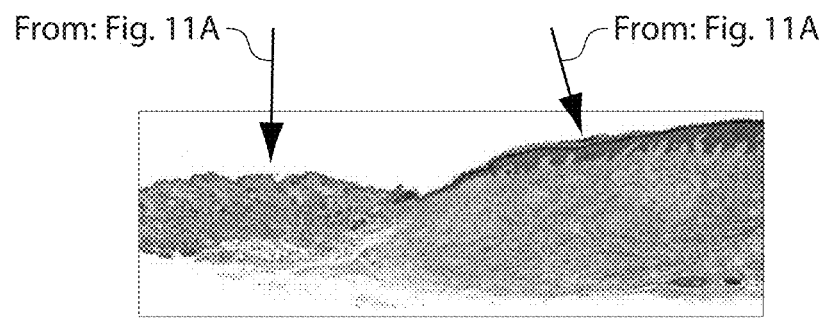
Figure 11C:
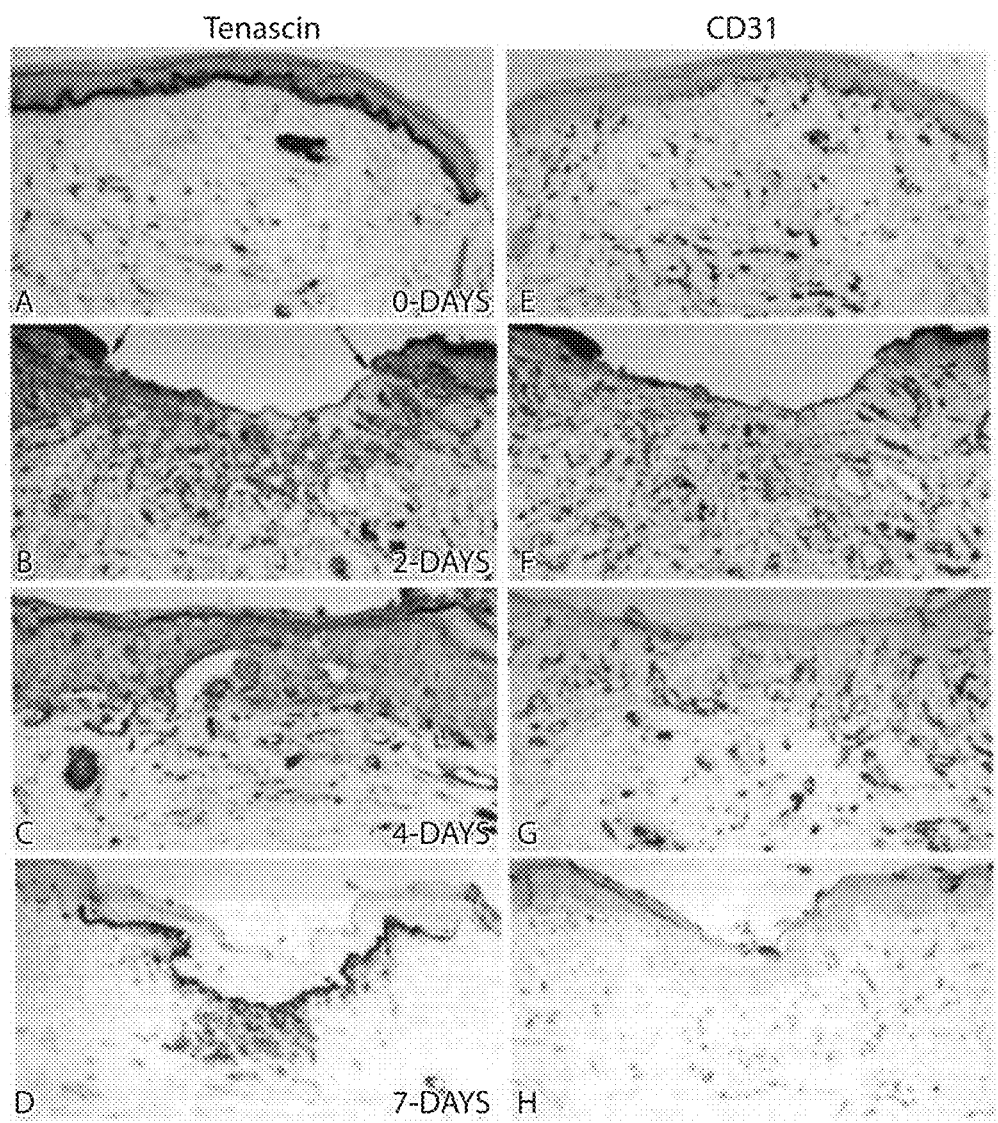

While mouse models are widely employed for the study of human disease, there are substantial differences in the wound healing process between human and non-human species[31]. For this reason, an alternative model in which full-thickness human skin grafts are transplanted onto immunodeficient mice[32] were used. In this model, the skin grafts closely resemble human skin histologically and maintain their human phenotype for at least 3 months. Discarded normal adult skin samples removed during plastic surgery were used for human skin grafting onto 8 week-old immunodeficient NSG mice (FIG. 11A, B). Wounding of the human skin xenograft resulted in a normal human wound healing pattern as shown in FIG. 11C.

Figure 12:
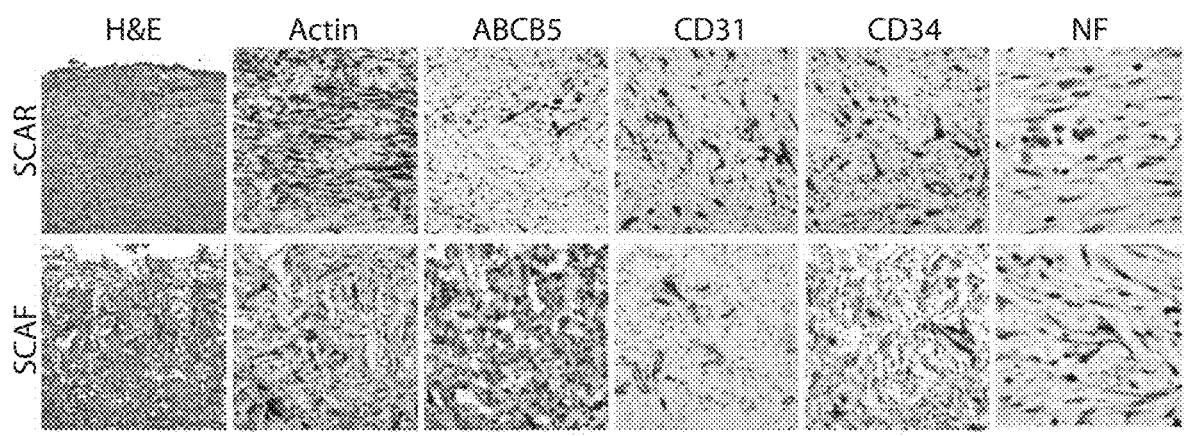
FIG. 12. Role of ABCB5 in human regenerative wound healing. Comparative studies examining the immunohistochemical profiles of healing responses consequent to scar formation and INTEGRA® scaffold-induced regeneration (scar v. scaf) may be ascertained (note striking re-alignment of actin-expressing myofibroblasts and markedly enhanced expression of ABCB5+ dermal cells in wound bearing the scaffold).

In addition, effects of INTEGRA® scaffold transplantation on regenerative wound healing in human patients was examined in biopsies obtained from either non-grafted wounds (FIG. 12, upper panels), or from human patient wounds transplanted with INTEGRA® scaffold grafts (FIG. 12, lower panels). Comparative analyses revealed immunohistochemical profiles of healing responses consequent to either scar formation (no INTEGRA®, FIG. 12, upper panels) or scaffold-induced regeneration, characterized by re-alignment of actin-expressing myofibroblasts and markedly enhanced expression of ABCB5+ dermal cells in wounds bearing the scaffold (INTEGRA®, FIG. 12, lower panels).

These results show that INTEGRA® scaffold grafting and resultant mobilization of ABCB5+ dermal MSC preferentially induces regenerative wound healing as opposed to wound healing via scar formation. Thus, human ABCB5+ dermal MSC significantly and selectively further enhance INTEGRA®-mediated regenerative wound healing (FIG. 10), and demonstrate therapeutic efficacy of human ABCB5+ dermal MSC/INTEGRA® scaffold co-grafting in the translationally most relevant human cutaneous wound healing experiments.

Dermal mesenchymal stem cells are required to provide a balance whereby normal healing responses occur in an orderly manner, resulting in gradual wound closure and physiologic scar formation. We anticipate that impaired dermal stem cell function in Abcb5 KO mice will lead to abnormal wound healing responses, which can be either insufficient healing or excessive healing. Deficient healing could be manifested as either subcutaneous tissue loss as observed in decubitus ulcer, or failure of re-epithealization as observed in venous ulcer, or necrosis-infection combination as observed in diabetic ulcer. Histologically, deficient wound healing could be characterized by excessive neutrophilic infiltration and increased MMP-9 collagenase secretion leading to collagen destruction[3]. Contrary, hypertrophic scars are characterized by increased collagen deposition due to an amplified inflammatory response with resultant overproduction of growth factors, including TGF-ß[58].

REFERENCES

1. Frank, N. Y. et al. Regulation of progenitor cell fusion by ABCB5 P-glycoprotein, a novel human ATP-binding cassette transporter. *J Biol Chem* 278, 47156-65 (2003).
2. Ko, S. H. et al. The role of stem cells in cutaneous wound healing: what do we really know? *Plast Reconstr Surg* 127 Suppl 1, 10S-20S.
3. Diegelmann, R. F. & Evans, M. C. Wound healing: an overview of acute, fibrotic and delayed healing. *Front Biosci* 9, 283-9 (2004).
4. Sarkar, A., Tatlidede, S., Scherer, S. S., Orgill, D. P. & Berthiaume, F. Combination of stromal cell-derived factor-1 and collagen-glycosaminoglycan scaffold delays contraction and accelerates reepithelization of dermal wounds in wild-type mice. *Wound Repair Regen* 19, 71-9.
5. Yannas, I. V., Lee, E., Orgill, D. P., Skrabut, E. M. & Murphy, G. F. Synthesis and characterization of a model extracellular matrix that induces partial regeneration of adult mammalian skin. *Proc Natl Acad Sci USA* 86, 933-7 (1989).
6. Yannas, I. V., Orgill, D. P. & Burke, J. F. Template for skin regeneration. *Plast Reconstr Surg* 127 Suppl 1, 60S-70S.
7. Badiavas, E. V. & Falanga, V. Treatment of chronic wounds with bone marrow-derived cells. *Arch Dermatol* 139, 510-6 (2003).
8. Falanga, V. et al. Autologous bone marrow-derived cultured mesenchymal stem cells delivered in a fibrin spray accelerate healing in murine and human cutaneous wounds. *Tissue Eng* 13, 1299-312 (2007).
9. Naysaria, H. A., Ojeh, N. O., Moiemen, N., Griffiths, M. A. & Frame, J. D. Reepithelialization of a full-thickness burn from stem cells of hair follicles micrografted into a tissue-engineered dermal template (Integra). *Plast Reconstr Surg* 113, 978-81 (2004).
10. Schurr, M. J. et al. Phase I/II clinical evaluation of StrataGraft: a consistent, pathogen-free human skin substitute. *J Trauma* 66, 866-73; discussion 873-4 (2009).
11. Toma, J. G. et al. Isolation of multipotent adult stem cells from the dermis of mammalian skin. *Nat Cell Biol* 3, 778-84 (2001).
12. Toma, J. G., McKenzie, I. A., Bagli, D. & Miller, F. D. Isolation and characterization of multipotent skin-derived precursors from human skin. *Stem Cells* 23, 727-37 (2005).
13. Fernandes, K. J. et al. A dermal niche for multipotent adult skin-*derived precursor cells. Nat Cell Biol* 6, 1082-93 (2004).
14. Bartsch, G. et al. Propagation, expansion, and multilineage differentiation of human somatic stem cells from dermal progenitors. *Stem Cells Dev* 14, 337-48 (2005).
15. Biernaskie, J. A., McKenzie, I. A., Toma, J. G. & Miller, F. D. Isolation of skin-derived precursors (SKPs) and differentiation and enrichment of their Schwann cell progeny. *Nat Protoc* 1, 2803-12 (2006).
16. Chen, F. G. et al. Clonal analysis of nestin(-) vimentin (+) multipotent fibroblasts isolated from human dermis. *J Cell Sci* 120, 2875-83 (2007).
17. Lavoie, J. F. et al. Skin-derived precursors differentiate into skeletogenic cell types and contribute to bone repair. *Stem Cells Dev* 18, 893-906 (2009).
18. Kuroda, Y. et al. Unique multipotent cells in adult human mesenchymal cell populations. *Proc Natl Acad Sci USA* 107, 8639-43.
19. Wilson, B. J. et al. ABCB5 identifies a therapy-refractory tumor cell population in colorectal cancer patients. *Cancer Res* 71, 5307-16 (2011).
20. Frank, N. Y. et al. VEGFR-1 expressed by malignant melanoma-initiating cells is required for tumor growth. *Cancer Res* 71, 1474-85 (2011).
21. Ma, J. et al. Isolation of tumorigenic circulating melanoma cells. *Biochem Biophys Res Commun* 402, 711-7.
22. Schatton, T. et al. Modulation of T-cell activation by malignant melanoma initiating cells. *Cancer Res* 70, 697-708.
23. Frank, N.Y. & Frank, M. H. ABCB5 gene amplification in human leukemia cells. *Leuk Res* 33, 1303-5 (2009).
24. Schatton, T. et al. Identification of cells initiating human melanomas. *Nature* 451, 345-9 (2008).
25. Frank, N. Y. et al. ABCB5-mediated doxorubicin transport and chemoresistance in human malignant melanoma. *Cancer Res* 65, 4320-33 (2005).
26. Kim, S. et al. Identification of human ABCB5+ dermal progenitor cells with multipotent differentiation plasticity. in *Society of Investigative Dermatology,* 2010 Annual Meeting Vol. 130 (Supplement 1S) S107 (Abstract 642). (Journal of Investigative Dermatology Atlanta, 2010).
27. Cheung, S. T., Cheung, P. F., Cheng, C. K., Wong, N.C. & Fan, S. T. Granulin-epithelin precursor and ATP-dependent binding cassette (ABC)B5 regulate liver cancer cell chemoresistance. *Gastroenterology* 140, 344-55.
28. Frank, N.Y., Schatton, T. & Frank, M. H. The therapeutic promise of the cancer stem cell concept. *J Clin Invest* 120, 41-50.

29. Gazzaniga, P. et al. CD133 and ABCB5 as stem cell markers on sentinel lymph node from melanoma patients. *Eur J Surg Oncol* 36, 1211-4.
30. Sharma, B. K., Manglik, V. & Elias, E. G. Immunoexpression of human melanoma stem cell markers in tissues at different stages of the disease. *J Surg Res* 163, e11-5.
31. Cohen, I. K. & Mast, B. A. Models of wound healing. *J Trauma* 30, S149-55 (1990).
32. Yan, H. C. et al. Human/severe combined immunodeficient mouse chimeras. An experimental in vivo model system to study the regulation of human endothelial cell-leukocyte adhesion molecules. *J Clin Invest* 91, 986-96 (1993).
33. Gottesman, M. M. How cancer cells evade chemotherapy: sixteenth Richard and Hinda Rosenthal Foundation Award Lecture. *Cancer Res* 53, 747-54 (1993).
34. Bosch, I., Dunussi-Joannopoulos, K., Wu, R. L., Furlong, S. T. & Croop, J. Phosphatidylcholine and phosphatidylethanolamine behave as substrates of the human MDR1 P-glycoprotein. Biochemistry 36, 5685-94 (1997).
35. Frank, M. H. et al. Specific MDR1 P-glycoprotein blockade inhibits human alloimmune T cell activation in vitro. *J Immunol* 166, 2451-9 (2001).
36. van Helvoort, A. et al. MDR1 P-glycoprotein is a lipid translocase of broad specificity, while MDR3 P-glycoprotein specifically translocates phosphatidylcholine. *Cell* 87, 507-17 (1996).
37. Bunting, K. D., Galipeau, J., Topham, D., Benaim, E. & Sorrentino, B. P. Effects of retroviral-mediated MDR1 expression on hematopoietic stem cell self-renewal and differentiation in culture. *Ann N Y Acad Sci* 872, 125-40; discussion 140-1 (1999).
38. Randolph, G. J. et al. A physiologic function for p-glycoprotein (MDR-1) during the migration of dendritic cells from skin via afferent lymphatic vessels. *Proc Natl Acad Sci USA* 95, 6924-9 (1998).
39. Gollapud, S. & Gupta, S. Anti-P-glycoprotein antibody-induced apoptosis of activated peripheral blood lymphocytes: a possible role of P-glycoprotein in lymphocyte survival. *J Clin Immunol* 21, 420-30 (2001).
40. Johnstone, R. W., Ruefli, A. A., Tainton, K. M. & Smyth, M. J. A role for P-glycoprotein in regulating cell death. *Leuk Lymphoma* 38, 1-11 (2000).
41. Chaudhary, P. M. & Roninson, I. B. Expression and activity of P-glycoprotein, a multidrug efflux pump, in human hematopoietic stem cells. *Cell* 66, 85-94 (1991).
42. Zhou, S. et al. The ABC transporter Bcrp1/ABCG2 is expressed in a wide variety of stem cells and is a molecular determinant of the side-population phenotype. *Nat Med* 7, 1028-34 (2001).
43. Spangrude, G. J., Brooks, D. M. & Tumas, D. B. Long-term repopulation of irradiated mice with limiting numbers of purified hematopoietic stem cells: in vivo expansion of stem cell phenotype but not function. *Blood* 85, 1006-16 (1995).
44. Zijlmans, J. M. et al. Modification of rhodamine staining allows identification of hematopoietic stem cells with preferential short-term or long-term bone marrow-repopulating ability. *Proc Natl Acad Sci USA* 92, 8901-5 (1995).
45. Goodell, M. A., Brose, K., Paradis, G., Conner, A. S. & Mulligan, R. C. Isolation and functional properties of murine hematopoietic stem cells that are replicating in vivo. *J Exp Med* 183, 1797-806 (1996).
46. Goodell, M. A. et al. Dye efflux studies suggest that hematopoietic stem cells expressing low or undetectable levels of CD34 antigen exist in multiple species. *Nat Med* 3, 1337-45 (1997).
47. Leemhuis, T. et al. Isolation of primitive human bone marrow hematopoietic progenitor cells using Hoechst 33342 and Rhodamine 123. *Exp Hematol* 24, 1215-24 (1996).
48. Hutcheson, D. A. & Kardon, G. Genetic manipulations reveal dynamic cell and gene functions: Cre-ating a new view of myogenesis. *Cell Cycle* 8, 3675-8 (2009).
49. Lakso, M. et al. Efficient in vivo manipulation of mouse genomic sequences at the zygote stage. *Proc Natl Acad Sci USA* 93, 5860-5 (1996).
50. Cotsarelis, G., Sun, T. T. & Lavker, R. M. Label-retaining cells reside in the bulge area of pilosebaceous unit: implications for follicular stem cells, hair cycle, and skin carcinogenesis. *Cell* 61, 1329-37 (1990).
51. Bickenbach, J. R. Identification and behavior of label-retaining cells in oral mucosa and skin. *J Dent Res* 60 Spec No C, 1611-20 (1981).
52. Morris, R. J., Fischer, S. M. & Slaga, T. J. Evidence that the centrally and peripherally located cells in the murine epidermal proliferative unit are two distinct cell populations. *J Invest Dermatol* 84, 277-81 (1985).
53. Erba, P., Ogawa, R., Vyas, R. & Orgill, D. P. The reconstructive matrix: a new paradigm in reconstructive plastic surgery. *Plast Reconstr Surg* 126, 492-8.
54. Peng, C. et al. Lack of FGF-7 Further Delays Cutaneous Wound Healing in Diabetic Mice. *Plast Reconstr Surg* 128, 673e-84e.
55. Schafer, M. & Werner, S. Cancer as an overhealing wound: an old hypothesis revisited. *Nat Rev Mol Cell Biol* 9, 628-38 (2008).
56. Tepper, O. M. et al. Adult vasculogenesis occurs through in situ recruitment, proliferation, and tubulization of circulating bone marrow-derived cells. *Blood* 105, 1068-77 (2005).
57. Lau, K., Paus, R., Tiede, S., Day, P. & Bayat, A. Exploring the role of stem cells in cutaneous wound healing. *Exp Dermatol* 18, 921-33 (2009).
58. Colwell, A. S., Phan, T. T., Kong, W., Longaker, M. T. & Lorenz, P. H. Hypertrophic scar fibroblasts have increased connective tissue growth factor expression after transforming growth factor-beta stimulation. *Plast Reconstr Surg* 116, 1387-90; discussion 1391-2 (2005).

All references cited herein are fully incorporated by reference. Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:
1. A method for tissue engineering, comprising seeding a biological tissue scaffold with ABCB5(+) stem cells, maintaining the scaffold under conditions such that tissue is formed, and implanting the seeded scaffold at a site of a tissue defect,
wherein the scaffold is a porous matrix of cross-linked collagen and glycosaminoglycan and wherein the scaffold includes a separate semi-permeable layer,
wherein at least 99% of the total cells present in the scaffold are ABCB5(+) stem cells, and wherein the ABCB5(+) stem cells are not treated with a soluble cytokine ex-vivo or in vitro prior to implantation.

2. The method of claim 1, wherein the ABCB5+ stem cells are ABCB5+ dermal mesenchymal stem cells.

3. The method of claim 1, wherein the ABCB5+ stem cells are ABCB5+ ocular stem cells.

4. The method of claim 1, wherein the collagen glycosaminoglycan scaffold is selected from the group of materials consisting of chondroitin 6-sulfate, chondroitin 4-sulfate, heparin, heparin sulfate, keratan sulfate, dermatan sulfate, chitin and chitosan.

5. The method of claim 1, wherein the collagen is bovine tendon collagen.

6. The method of claim 1, wherein the semi-permeable layer is polysiloxane.

7. The method of claim 6, wherein the scaffold is a Meshed Bilayer Wound Matrix.

8. The method of claim 1, wherein the scaffold has a pore size of about 10-500 micrometers.

9. The method of claim 1, wherein the scaffold has a pore size of about 50-350 micrometers.

10. The method of claim 1, wherein the scaffold has a pore size of about 70-200 micrometers.

\* \* \* \* \*